US010166293B2

(12) United States Patent
Liu et al.

(10) Patent No.: US 10,166,293 B2
(45) Date of Patent: *Jan. 1, 2019

(54) REDUCED-VISCOSITY CONCENTRATED PROTEIN FORMULATIONS

(71) Applicants: Genentech, Inc., South San Francisco, CA (US); Novartis AG, Basel (CH)

(72) Inventors: Jun Liu, Pacifica, CA (US); Steven J. Shire, Belmont, CA (US)

(73) Assignees: Genentech, Inc., South San Francisco, CA (US); Novartis AG, Basel (CH)

( * ) Notice: Subject to any disclaimer, the term of this patent is extended or adjusted under 35 U.S.C. 154(b) by 0 days.

This patent is subject to a terminal disclaimer.

(21) Appl. No.: 14/201,346

(22) Filed: Mar. 7, 2014

(65) Prior Publication Data

US 2015/0044198 A1    Feb. 12, 2015

Related U.S. Application Data

(60) Continuation of application No. 13/306,846, filed on Nov. 29, 2011, now Pat. No. 8,703,126, which is a continuation of application No. 11/611,751, filed on Dec. 15, 2006, now Pat. No. 8,142,776, which is a continuation of application No. 11/068,553, filed on Feb. 28, 2005, now Pat. No. 7,666,413, which is a division of application No. 09/971,511, filed on Oct. 4, 2001, now Pat. No. 6,875,432.

(60) Provisional application No. 60/293,834, filed on May 24, 2001, provisional application No. 60/240,107, filed on Oct. 12, 2000.

(51) Int. Cl.
| | |
|---|---|
| *A61K 47/02* | (2006.01) |
| *A61K 39/395* | (2006.01) |
| *C07K 16/42* | (2006.01) |
| *A61K 9/19* | (2006.01) |
| *A61K 39/00* | (2006.01) |

(52) U.S. Cl.
CPC ........... *A61K 47/02* (2013.01); *A61K 9/19* (2013.01); *A61K 39/39566* (2013.01); *A61K 39/39591* (2013.01); *C07K 16/4291* (2013.01); *A61K 2039/505* (2013.01)

(58) Field of Classification Search
None
See application file for complete search history.

(56) References Cited

U.S. PATENT DOCUMENTS

| | | |
|---|---|---|
| 4,075,193 A | 2/1978 | Campbell et al. |
| 4,093,606 A | 6/1978 | Coval |
| 4,374,763 A | 2/1983 | Takagi et al. |
| 4,499,073 A | 2/1985 | Tenold |
| 4,877,608 A | 10/1989 | Lee et al. |
| 4,940,782 A | 7/1990 | Rup et al. |
| 5,096,885 A | 3/1992 | Pearlman et al. |
| 5,215,743 A | 6/1993 | Singh et al. |
| 5,252,480 A | 10/1993 | Yokota et al. |
| 5,262,296 A | 11/1993 | Ogawa et al. |
| 5,328,694 A | 12/1994 | Schwinn |
| 5,399,670 A | 3/1995 | Bhattacharya et al. |
| 5,580,856 A | 12/1996 | Prestrelski et al. |
| 5,608,038 A | 3/1997 | Eibl et al. |
| 5,612,315 A | 3/1997 | Pikal et al. |
| 5,849,700 A | 12/1998 | Sorenson et al. |
| 5,871,736 A | 2/1999 | Bruegger et al. |
| 5,994,511 A | 11/1999 | Lowman et al. |
| 6,013,773 A | 1/2000 | Kobayashi et al. |
| 6,037,453 A | 3/2000 | Jardieu et al. |
| 6,096,872 A | 8/2000 | Van Holten et al. |
| 6,172,213 B1 | 1/2001 | Lowman et al. |
| 6,252,055 B1 | 6/2001 | Relton |
| 6,267,958 B1 | 7/2001 | Andya et al. |
| 6,290,957 B1 | 9/2001 | Lowman et al. |
| 6,329,509 B1 | 12/2001 | Jardieu et al. |
| 6,440,426 B1 | 8/2002 | Wheeler et al. |
| 6,525,102 B1 | 2/2003 | Chen et al. |
| 6,541,606 B2 | 4/2003 | Margolin et al. |
| 6,638,913 B1 | 10/2003 | Speck et al. |
| 6,682,735 B2 | 1/2004 | Lowman et al. |
| 6,685,939 B2 | 2/2004 | Jardieu et al. |
| 6,685,940 B2 | 2/2004 | Andya et al. |
| 6,699,472 B2 | 3/2004 | Jardieu et al. |
| 6,723,833 B1 | 4/2004 | Lowman et al. |
| 6,875,432 B2 | 4/2005 | Liu et al. |
| 7,157,085 B2 | 1/2007 | Lowman et al. |
| 7,666,413 B2 | 2/2010 | Liu et al. |

(Continued)

FOREIGN PATENT DOCUMENTS

| | | |
|---|---|---|
| CA | 2138853 A1 | 6/1995 |
| CA | 2423227 A1 | 4/2002 |

(Continued)

OTHER PUBLICATIONS

Adelroth, E. et al. (Aug. 2000). "Recombinant Humanized mAb-E25, an Anti-IgE mAb, in Birch Pollen-induced Seasonal Allergic Rhinitis," *J. Allergy Clin. Immunol.* 106(2):253-259, Abstract Only.
American Hospital Formulary Service. (1998). "Immune Globulin," *AHFS 98 Drug Information*, American Hospital Formulary Service, pp. 2708-2717.
Anonymous. "Calculation of the Salt and/or Buffer Concentration of Beriglobin®," Excerpt/Analysis from WO 97/04801, two pages.
Anonymous. (May 14, 2004). "Gammanorm® Receives Approval in 9 More Countries," Octapharma News, located at <http://www.octapharma.com/corporate/01_octapharma_news/02_news_2004/051604/ . . . >, last visited Jun. 16, 2010, two pages.
Anonymous. Excerpt from Irish Marking Authorization Application in document dated Jan. 13, 1983, 2010, Product Description of "Gammabulin," four pages.

(Continued)

*Primary Examiner* — Yunsoo Kim
(74) *Attorney, Agent, or Firm* — Morrison & Foerster LLP

(57) ABSTRACT

The present application concerns concentrated protein formulations with reduced viscosity, which are particularly suitable for subcutaneous administration. The application further concerns a method for reducing the viscosity of concentrated protein formulations.

58 Claims, 4 Drawing Sheets

(56) References Cited

U.S. PATENT DOCUMENTS

| | | | |
|---|---|---|---|
| 8,142,776 B2* | 3/2012 | Liu | A61K 9/0019 424/130.1 |
| 8,318,161 B2 | 11/2012 | Esue | |
| 8,703,126 B2 | 4/2014 | Liu et al. | |
| 8,961,964 B2* | 2/2015 | Liu | A61K 9/0019 424/130.1 |
| 2002/0045571 A1 | 4/2002 | Liu et al. | |
| 2003/0092607 A1 | 5/2003 | Carpenter et al. | |
| 2003/0113316 A1 | 6/2003 | Kaisheva et al. | |
| 2003/0138417 A1 | 7/2003 | Kaisheva et al. | |
| 2004/0019243 A1 | 1/2004 | Nightingale et al. | |
| 2004/0191243 A1 | 9/2004 | Chen et al. | |
| 2004/0197324 A1 | 10/2004 | Lui et al. | |
| 2005/0158303 A1 | 7/2005 | Liu et al. | |
| 2005/0175603 A1 | 8/2005 | Liu et al. | |
| 2006/0051347 A1 | 3/2006 | Winter | |
| 2006/0127395 A1 | 6/2006 | Arvinte et al. | |
| 2007/0053900 A1 | 3/2007 | Liu et al. | |
| 2007/0086995 A1 | 4/2007 | Liu et al. | |
| 2007/0116700 A1 | 5/2007 | Liu et al. | |
| 2008/0071063 A1 | 3/2008 | Allan et al. | |
| 2009/0060906 A1 | 3/2009 | Barry et al. | |
| 2009/0169544 A1 | 7/2009 | Nilsson et al. | |
| 2009/0280129 A1 | 11/2009 | Liu et al. | |
| 2010/0158898 A1 | 6/2010 | Liu et al. | |
| 2010/0239567 A1 | 9/2010 | Esue | |
| 2012/0064086 A1 | 3/2012 | Liu et al. | |
| 2012/0076783 A1 | 3/2012 | Liu et al. | |
| 2016/0367675 A1 | 12/2016 | Liu et al. | |

FOREIGN PATENT DOCUMENTS

| | | |
|---|---|---|
| CA | 2423227 C | 4/2002 |
| CH | 684 164 A5 | 7/1994 |
| EP | 0 025 719 A2 | 3/1981 |
| EP | 0 117 060 A2 | 8/1984 |
| EP | 0 117 060 A3 | 8/1984 |
| EP | 0 187 712 A2 | 7/1986 |
| EP | 0 303 746 A1 | 2/1989 |
| EP | 0 303 746 B1 | 2/1989 |
| EP | 0 303 746 B2 | 2/1989 |
| EP | 0 391 444 A2 | 10/1990 |
| EP | 0 391 444 A3 | 10/1990 |
| EP | 0 531 539 A1 | 3/1993 |
| EP | 0 531 539 B1 | 3/1993 |
| EP | 0 597 101 A1 | 5/1994 |
| EP | 0 597 101 B1 | 5/1994 |
| EP | 0 661 060 A2 | 7/1995 |
| EP | 0 661 060 A3 | 7/1995 |
| EP | 0 661 060 B1 | 7/1995 |
| EP | 0 764 447 A2 | 3/1997 |
| EP | 0 787 497 A2 | 8/1997 |
| EP | 0 787 497 A3 | 8/1997 |
| EP | 0 841 067 A1 | 5/1998 |
| EP | 0 841 067 B1 | 5/1998 |
| EP | 0 909 564 A1 | 4/1999 |
| EP | 0 909 564 B1 | 4/1999 |
| EP | 1 197 221 A1 | 4/2002 |
| EP | 1 197 221 B1 | 4/2002 |
| EP | 1 325 751 A1 | 7/2003 |
| EP | 1 356 829 A2 | 10/2003 |
| GB | 2 030 150 A | 4/1980 |
| JP | 5-504342 A | 7/1993 |
| JP | 7-206709 A | 8/1995 |
| JP | 11-510170 A | 9/1999 |
| JP | 2001-503781 | 3/2001 |
| WO | WO-89/11297 A1 | 11/1989 |
| WO | WO-90/11091 A1 | 10/1990 |
| WO | WO-92/17207 A1 | 10/1992 |
| WO | WO-93/04173 A1 | 3/1993 |
| WO | WO-93/05799 A1 | 4/1993 |
| WO | WO-95/23854 A1 | 9/1995 |
| WO | WO-96/20202 A1 | 7/1996 |
| WO | WO-97/04801 A1 | 2/1997 |
| WO | WO-97/04807 A1 | 2/1997 |
| WO | WO-97/26862 A2 | 7/1997 |
| WO | WO-97/26909 A1 | 7/1997 |
| WO | WO-97/28828 A1 | 8/1997 |
| WO | WO-97/45140 A1 | 12/1997 |
| WO | WO-98/22136 A2 | 5/1998 |
| WO | WO-98/22136 A3 | 5/1998 |
| WO | WO-99/01556 A2 | 1/1999 |
| WO | WO-00/15260 A1 | 3/2000 |
| WO | WO-01/24814 A1 | 4/2001 |
| WO | WO-02/12501 A2 | 2/2002 |
| WO | WO-02/030463 A2 | 4/2002 |
| WO | WO-02/30464 A1 | 4/2002 |
| WO | WO-02/072636 A2 | 9/2002 |
| WO | WO-02/072636 A3 | 9/2002 |
| WO | WO-02/096457 A2 | 12/2002 |
| WO | WO-02/096457 A3 | 12/2002 |
| WO | WO-2004/030607 A2 | 4/2004 |
| WO | WO-2004/030607 A3 | 4/2004 |
| WO | WO-2004/091658 A1 | 10/2004 |
| WO | WO-2006/065746 A2 | 6/2006 |
| WO | WO-2006/065746 A3 | 6/2006 |

OTHER PUBLICATIONS

Anonymous. Properties of "Beriglobin," Excerpt/Analysis from WO 97/04801, one page.
Anonymous. Vikositäts-Tabelle., one page. English Description: Viscosity table, the compilation in accordance with D17 (this table) shows the viscosities of the preparations mentioned in citations D3 (EP 0 187 712) and D4 (EP 0 025 719) and the preparations in accordance with D5 (Austria-Codex: Beriglobin) and D8 (Pharmacia: Gammanorm).
Anonymous. Vikositäts-Tabelle, with English Translation, two pages.
Arakawa et al. (1991). "Protein-Solvent Interactions in Pharmaceutical Formulations" *Pharmaceutical Research* 8(3):285-291.
Austria-Codex. (1997). Definition of "Beriglobin" in Austria-Codex Fachinformation, pp. 354-355. (Foreign Language.).
Austria-Codex. (1997). Definition of "Beriglobin" in Austria-Codex Fachinformation, pp. 354-355. (With English Translation, four pages).
Austria-Codex. (1997). Definition of "Berirab" in Austria-Codex Fachinformation, p. 361. (Foreign Language).
Austria-Codex. (1997). Definition of "Berirab" in Austria-Codex Fachinformation, pp. 360-361. (With English Translation, four pages).
Austria-Codex. (1997). Definition of "Tetagam" in Austria-Codex Fachinformation, pp. 3198-3199. (Foreign Language).
Austria-Codex. (1997). Definition of "Tetagam" in Austria-Codex Fachinformation, pp. 3198-3199. (With English Translation, five pages).
Bam et al. (1995). "Stability of Protein Formulations: Investigation of Surfactant Effects by a Novel EPR Spectroscopic Technique," *Pharmaceutical Research* 12:2-11.
Bayer Corporation. (Oct. 2000). Product Description of BayHep B®, seven pages.
Bayer NZ (Oct. 5, 2004). Datasheet: BayHep B, 10 pages.
Behring, CSL. Package Insert Product Description of "Beriglobin®," two pages. (Foreign Language.), 2008.
Behring, CSL. (2008). Package Insert Product Description of "Beriglobin®," with English Translation, six pages.
Benninger, G.W. et al. (Aug. 1971). "Aggregation Phenomenon in an IgG Multiple Myeloma Resulting in the Hyperviscosity Syndrome," *American Journal of Medicine* 51:287-293.
Booth, F. (1950). "The Electroviscous Effect for Suspensions of Solid Sperical Particles," *Proc. Roy. Soc.* (London) A203:533-551.
Breen, E.D. et al. (Sep. 2001). "Effect of Moisture on the Stability of a Lyophilized Humanized Monoclonal Antibody Formulation" *Pharmaceutical Research* 18(9):1345-1353.
British Pharmacopoeia. (Dec. 1, 1999). vol. II, pp. A110, Appendix I D, 2101, and A82 Appendix I A, four pages.
Buzzell, J.G. et al. (Sep. 1956). "The Effect of Charge and Ionic Strength on the Viscosity of Ribonuclease," *J. Phys. Chem.* 60:1204-1207.

(56) References Cited

OTHER PUBLICATIONS

Capra, J.D. et al. (1970). "Aggregation of γG3 Proteins: Relevance to the Hyperviscosity Syndrome," *The Journal of Clinical Investigation* 49:610-621.

Carpenter, J.F. et al. (1997). "Rational Design of Stable Lyophilized Protein Formulations: Some Practical Advice," *Pharmaceutical Research* 14(8):969-975.

Casale, T.B. (Oct. 2001). "Anti-Immunoglobulin E (Omalizumab) Therapy in Seasonal Allergic Rhinitis," *Am. J. Respir. Crit. Care Med.* 164(8):S18-S21, located at <http://ajrccm.atsjournals.org/cgi/content/full/164/8/S1/S18>, last visited Jun. 7, 2010, 7 pages.

Casolaro, V. et al. (1993). "Release from Human Basopbils and Mast Cells" *J. of Pharmacology and. Experimental Therapeutics* 267(3) :1375-1385.

Centocor, Inc. (Aug. 12, 1998). Product Description of Remicade™ Infliximab for IV Injection, 12 pages.

Chang, L. (Sep. 2009). "Mechanisms of Protein Stabilization in the Solid State" *Journal of Pharmaceutical Sciences* 98(9):2886-2908.

Chen, B. et al. (Dec. 2003). "Influence of Histidine on the Stability and Physical Properties of a Fully Human Antibody in Aqueous and Solid Forms," *Pharmaceutical Research* 20(12):1952-1960.

Chick, H. (1914). Chapter XXXIV, "The Viscosity of Protein Solutions. II. Pseudoglobulin and Euglobulin (Horse)," *Biochem J.* 8:261-280.

Cleland, J.L. et al. (1993). "The Development of Stable Protein Formulations: A Close Look at Protein Aggregation, Deamidation, and Oxidation" *Critical Reviews in Therapeutic Drug Carrier Systems* 10(4):307-377.

Cleland, J.L. et al. (1995). "Development of Stable Protein Formulations for Microencapsulation in Biodegradable Polymers," *Proceed. Intern. Symp. Control. Rel. Bioact. Mater.* 22:514-515.

Corne, J. et al. (1997). "The Effect of Intravenous Administtration of a Chimeric Anti-IgE Antibody on Serum IgE Levels in Atopic Subjects: Efficacy, Smacokinetics," *J. Clin. Invest.* 99(5):879-887.

Dalakas, M.C. (Feb. 1994). "High-dose Intravenous Immunoglobulin and Serum Viscosity: Risk of Precipitating Thromboembolic Events," *Neurology* 44:223-226.

Dalakas, M.C. (May 1, 1997). "Intravenous Immune Globulin Therapy for Neurologic Diseases," *Annals of Internal Medicine* 126(9):721-730.

Dalakas, M.C. (1998). "Mechanism of Action of Intravenous Immunoglobulin and Therapeutic Considerations in the Treatment of Autoimmune Neurologic Diseases," *Neurology* 51(Suppl. 5):S2-S8.

Daugherty, A.L. et al. (2006). "Formulation and Delivery Issues for Monoclonal Antibody Therapeutics," *Advanced Drug Delivery Reviews* 58:686-706.

Doutrelepont, J.M. et al. (1991). "Hyper IgE in Stimulatory Graft-versus-Host Disease: Role of Interleukin-4," *Clin. Exp. Immunol.* 83:133-136.

Draber, P. et al. (1995). "Stability of Monoclonal IgM Antibodies Freeze-Dried in the Presence of Trehalose," *Journal of Immunological Methods* 181(1):37-43.

Fachinfo-Service. (Oct. 2009). "Baxter: Subcuvia 160 g/l Injektionslösung," Fachinformation Rote Liste, three pages.

Fachinfo-Service. (Oct. 2009). "Package Circular: Baxter: Subcuvia 160 g/l Solution for Injection," Fachinformation Rote Liste, with English Translation, six pages.

Fachinfo-Service. (Apr. 2010). "CSL Behring: Beriglobin®," *Fachinformation Rote Liste*, three pages.

Fachinfo-Service. (Apr. 2010). "Package Circular: CSL Behring: Beriglobin®," Fachinformation Rote Liste, with English Translation, six pages.

Fahey, K.R. et al. (Dec. 1938). "The Viscosities of Solutions of the Proteins of Horse Serum," *Journal of American Chem. Society* 60:3039-3043.

Fahy, J.V. et al. (2007). "The effect of an anti-IgE monoclonal antibody on the early- and late-phase responses to allergen inhalation in asthmatic subjects", *Am. J. Respir Care Med.,* 155(6):1828-34.

Garidel, P. et al. (2009, pub. Apr. 16, 2009). "A thermodynamic Analysis of the Binding Interaction Between Polysorbate 20 and 80 With Human Serum Albumins and Immunoglobulins: A Contribution to Understand Colloidal Protein Stabilisation," *Biophysical Chemistry* 143:70-78.

Giles, R.L. et al. (1990). "Plastic Packaging Materials," Chapter 80 in *Remington's Pharmaceutical Sciences,* 18th Edition, Gennaro, A.R. ed., Mack Publishing Company: Easton, PA, p. 1499.

Gokarn, Y.R. et al. (Aug. 2008). "Self-Buffering Antibody Formulations," *Journal of Pharmaceutical Sciences* 97(8):3051-3066.

Haag, S. et al. (Oct. 2006). "Comparison of the Viscosity of Three Subcutaneous Immunoglobulin Brands (SCIG). Potential Implicatons for Clinical Use," Poster *presentation at XIIth Meeting of the European Society for Immunodeficiencies,* Oct. 4-7, 2006, Budapest, Hungary, two pages.

Haecker, G. et al. (1994). "Proliferative and Cytolytic Responses of Human γδ T Cells Display a Distinct Specificity Pattern," *Immunology* 81:564-566.

Hankinson, C.L. et al. (1941). "Electrokinetics XXV. The Electroviscous Effect. II in Systems of Calcium and Sodium Caseinates," *J. Phys. Chem.* 45(6):943-953.

Harris, R.J. et al. (2004). "Commercial Manufacturing Scale Formulation and Analytical Characterization of Therapeutic Recombinant Antibodies," *Drug Development Research* 61:137-154.

He, F. et al. (Apr. 2010, e-pub. Sep. 24, 2009). "High throughput Thermostability Screening of Monoclonal Antibody Formulations" *Journal of Pharmaceutical Sciences* 99(4):1707-1720.

Hess, E.L. et al. (May 20, 1950). "The Intrinsic Viscosity of Mixed Protein Systems, Including Studies of Plasma and Serum," *J. Gen. Physiol.* 33:511-523.

Holma, B. et al. (1989). "pH- and Protein-Dependent Buffer Capacity and Viscosity of Respiratory Mucus, Their Interrelationships and Influence on Health," *The Science of the Total Environment* 84:71-82.

Hudson, L. et al. (1980). *Practical Immunology,* Second Edition, Blackwell Scientific Publications, p. 336.

IDEC/Genentech. (Nov. 1997). Product Description of Rituxan™, two pages.

Immuno, Ltd. (Jan. 13, 1983). Letter from N. Berry to National Drugs Advisory Board re: Authorization to Market Gammabulin, one page.

Immuno, Ltd. (Dec. 20, 1991). Letter of Product Licence Applications for Tetabulin for GB and Ireland, three pages.

Immuno, Ltd. (Oct. 1997). Normal Immunoglobulin Injection B.P.: GAMMABULIN® Package Insert Product Description, two pages.

Immuno, Ltd. (Dec. 1997). GAMMABULIN®: Normal Immunoglobulin Injection B.P. Product Description, two pages.

International Search Report dated Jun. 19, 2002, for PCT Application No. PCT/US01/42487, filed Oct. 4, 2001, two pages.

Iwanaga, S. (1978). "1-2-1 Separation Method Making Use of Solubility," *New Lectures on Experimental Chemistry* 20(Biochemistry 1):14-26.

Jones, A. (1993). "Analysis of Polypeptides and Proteins," *Adv. Drug Delivery Rev.* 10:29-90.

Kalapathy, U. et al. (1996). "Alkali-Modified Soy Proteins: Effect of Salts and Disulfide Bond Cleavage on Adhesion and Viscosity," *JAOCS* 73(8):1063-1066.

Kanai, S. et al. (Oct. 2008). "Reversible Self-Association of a Concentrated Monoclonal Antibody Solution Mediated by Fab-Fab Interaction That Impacts Solution Viscosity," *Journal of Pharmaceutical Sciences* 97(10):4219-4227.

Katdare et al. Appendix: Formulations of Approved Protein Drugs in *Excipients for Protein Drugs, Excipient Development for Pharmaceutical Biotechnology and Drug Delivery Systems.* Gokarn et al. eds., pp. 307-331.

Kim, Y-C. et al. (1997). "Diffusivity, Viscosity, and Cluster Formation in Protein Solutions," *Biotechnol. Bioprocess Eng.* 2(1):64-67.

Kinekawa, Y-I. et al. (1998). "Effects of Salts on the Properties of Sols and Gels Prepared from Whey Protein Isolate and Process Whey Protein," *Journal of Dairy Science* 81(6):1532-1544.

Kistler, P. et al. (1962). "Large Scale Production of Human Plasma Fractions," *Vox Sang* 7:414-424.

(56) References Cited

OTHER PUBLICATIONS

Kochwa, S. et al. (Jan. 1966). "Aggregation of IgG Globulin in Vivo. II. Physicochemical Properties of the Isolated Protein," *Biochemistry* 5(1):277-285.
Lehninger, A.L. et al. (1993). "Amino Acids and Peptides," Chapter 5 in *Principles of Biochemistry*, Second Edition, Worth Publishers: New York, NY, pp. 111-122.
Letter dated Jan. 26, 2009 from Representative Mewburn Ellis in Response to Request for Oral Proceedings in EP Patent Application 01981824.4, six pages.
List, P.H. (1985). "Injektions- and Infusionszubereitungen," Chapter 18.4, in *Arzneiformenlehre*, 4th Edition, pp. 416-419. (Foreign Language).
List, P.H. (1985). "Injection and Infusion Preparations," Chapter 18.4, in *Pharmacy: Textbooks for Pharmacists*, 4th Edition, Scientific Publishers: Stuttgart, DE, pp. 416-419. (With English Translation, six pages).
Liu et al. (Sep. 2005). "Reversible Self-Association Increases the Viscosity of a Concentrated Monoclonal Antibody in Aqueous Solution" *Journal of Pharmaceutical Sciences* 94(9).
Loeb, J. (1921). "Dorman Equilibrium and the Physical Properties of Proteins," Chapter III, Viscosity, in *The Journal of General Physiology*, pp. 827-841.
Loeb, J. (1921). "Donnan Equilibrium and the Physical Properties of Proteins," Chapter IV, Viscosity, in *The Journal of General Physiology*, pp. 73-95.
Loeb, J. (1921). "Ion Series and the Physical Properties of Proteins," in Chapter III, the Action of Salts in Low Concentration, in *The Journal of General Physiology*, pp. 391-414.
MacKenzie, M.R. et al. (1970). "The Hyperviscosity Syndrome. I. In IgG Myeloma. The Role of Protein Concentration and Molecular Shape," *The Journal of Clinical Investigation* 49:15-20.
Mahler et al. (1966). *Biological Chemistry* Table 2.1, one page.
Manning et al. (1989). "Stability of Protein Pharmaceuticals" *Pharm. Res.* 6(11):903-918.
Martindale. (1993). Descriptions of "Normal Immunoglobins" in *Martindale the Extra Pharmacopoeia*, 30th Edition, Reynolds, J.E.F. ed., Pharmaceutical Press: London, England, pp. 1290-1294, 1302-1303, 1578, 1611, 1856.
Martindale. (1999). Descriptions of "Normal Immunoglobins" in *Martindale the Complete Drug Reference*, 32nd Edition, Parfitt, K. ed., Pharmaceutical Press: London, England, pp. 1522-1525, 1535, 1778, 1805, 1932, 2011.
Mattern, M. et al. (2009). "Formulation of Proteins in Vacuum-Dried Glasses. II. Process and Storage Stability in Sugar-Free Amino Acid Systems" *Pharmaceutical Development and Technology* 4(2):199-208.
Menjivar, J.A. et al. (1980). "Viscoelastic Effects in Concentrated Protein Dispersions," *Rheol. Acta* 19:212-219.
Merck Index (1983). 10th Ed., Merck &Co., Inc. pp. 797-798.
Middaugh, C.R. et al. (1992). "Protein Solubility," Chapter 4 in *Stability of Protein Pharmaceuticals, Part A: Chemical and Physical Pathways of Protein Degradation*, Ahern, T.J. et al. eds., Plenum Press: New York, NY, pp. 109-134.
Middleton, H.M. III (1979). "Intestinal Absorption of Pyridoxal-5'-Phosphate: Disappearance from Perfused Segments of Rat Jejunum in Vivo," *Journal of Nutrition* 109:975-981.
Milgrom, H. et al. (Dec. 23, 1999). "Treatment of Allergic Asthma with Monoclonal Anti-IgE Antibody. rhuMAb-E25 Study Group," *The New England Journal of Medicine* 341(26):1966-1973.
Milgrom, H. et al. (Aug. 2, 2001). "Treatment of Childhood Asthma With Anti-Immunoglobulin E Antibody (Omalizumab)," *Pediatrics* 108(2):1-10.
Monkos, K. (1997). "Concentration and Temperature Dependence of Viscosity in Lysozyme Aqueous Solutions," *Biochimica et Biophysica Acta* 1339:304-310.
Monkos, K. (2000). "Viscosity Analysis of the Temperature Dependence of the Solution Conformation of Ovalbumin," *Biophysical Chemistry* 85:7-16.
Monkos, K. et al. (1999). "A Comparative Study on Viscosity of Human, Bovine and Pig IgG Immunoglobulins in Aqueous Solutions," *International Journal of Biological Macromolecules* 26:155-159.
Nielsen, et al. (1995). "Stability of Freeze Dried Horseradish Peroxidase Conjugated Monoclonal Antibodies Used in Diagnostic Serology," *Journal of Immunoassay* 16(2):183-197.
Non-Final Office Action dated Dec. 21, 2010, for U.S. Appl. No. 12/197,005, filed Aug. 22, 2008, eight pages.
Notice of Opposition and Opposition Brief for EP 1 324 776: Abbott Bioresearch Center Patent Department, Jun. 16, 2010, 24 pages.
Notice of Opposition and Opposition Brief for EP 1 324 776: Maiwald, Jun. 16, 2010, 77 pages.
Notice of Opposition of EP 1 324 776: Ablynx N.V., Jun. 16, 2010, seven pages.
Notice of Opposition of EP 1 324 776: Arecor Limited, Jun. 15, 2010, five pages.
Notice of Opposition of EP 1 324 776: Baxter Healthcare SA, Jun. 16, 2010, six pages.
Notice of Opposition of EP 1 324 776: Boehringer Ingelheim Pharma GmbH & Co., Jun. 16, 2010, seven pages.
Notice of Opposition of EP 1 324 776: Maiwald/Eingabe, Jun. 16, 2010, one page.
Notice of Opposition of EP 1 324 776: Sanofi Aventis, Jun. 16, 2010, seven pages.
Notice of Opposition of EP 1 324 776: Synthon B.V., Jun. 16, 2010, six pages.
Notice of Opposition of EP 1 324 776: UCB Pharma S.A., Jun. 15, 2010, four pages.
Nydegger, U.E. (1996). "Safety and Side Effects of I.V. Immunoglobulin Therapy," *Clinical and Experimental Rheumatology* 14(Suppl. 15):S53-S57.
Octapharma. (Jan. 9, 2008). Product Description of Gammanorm, Octapharma, eight pages.
Office Action Response for EP Application No. 01981824.4 filed by Mewburn Ellis, dated Oct. 11, 2004, 14 pages.
Opposition Brief Filed by Ablynx N.V. in EP 1 324 776 filed on Jun. 16, 2010, 17 pages.
Opposition Brief Filed by Baxter Healthcare Corporation in EP 1 324 776 filed on Jun. 16, 2010, 39 pages.
Opposition Brief Filed by Boehringer Ingelheim Pharma in EP 1 324 776 filed on Jun. 16, 2010, 11 pages.
Opposition Brief Filed by Octapharma AG in EP 1 324 776 filed on Jun. 16, 2010, 11 pages. (English Language).
Opposition Brief Filed by Octapharma AG in EP 1 324 776 filed on Jun. 16, 2010, 14 pages. (German Language).
Opposition Brief Filed by Sanofi Aventis in EP 1 324 776 filed on Jun. 16, 2010, 12 pages. (English Language).
Opposition Brief Filed by Sanofi Aventis in EP 1 324 776 filed on Jun. 16, 2010, 13 pages. (French Language).
Opposition Brief Filed by Synthon in EP 1 324 776 filed on Jun. 16, 2010, nine pages.
Opposition Brief Filed by UCB CellTech in EP 1 324 776 filed Jun. 2010, 31 pages.
Opposition Brief Filed by UCB Pharma in EP 1 324 776, filed on Jun. 15, 2010, 23 pages.
Osmolalität: Osmolality Data of Antibody Solutions, one page. (Foreign Language).
Osmolalität: Osmolality Data of Antibody Solutions, with English Translation, two pages.
Patapoff, T.W. et al. (2009). "Polysorbate 20 Prevents the Precipitation of a Monoclonal Antibody During Shear" *Pharmaceutical Development and Technology* 14(6):659-664.
Pearlman et al. (1991). "Analysis of Protein Drugs," Chapter 6 in *Peptide and Protein Drug Delivery*, Vincent H. L. Lee ed., Marcel Dekker, Inc., pp. 247-301.
Pei "Immunoglobulinpräparate" located at <http://www.pei.de/cln_101/nn_158990/DE/arzneimittel/immunoglobuline/im-iv-sk/im-i . . . >, last visited Jun. 16, 2010, three pages. (Foreign Language).
Pei "Immunoglobulin Preparations" located at <http://www.pei.de/cln_101/nn_158990/DE/arzneimittel/immunoglobuline/im-iv-sk/im-i . . . >, last visited Jun. 16, 2010, with English Translation, six pages.

(56) References Cited

OTHER PUBLICATIONS

Perepetschkina, N.P. et al. (1986). "Some Specific Features of the Ultrafiltration of Immunobiologic Preparations," *The Mechnikov Central Research Institute of Vaccines and Serums*, pp. 1-6. (English Translation).

Perepetschkina, N.P. et al. (1986). "Zurnal Mikrobiologii, Epidemiologii I Imunobiologii," 6:46-50. (Russian Language).

Pharmacia. (Oct. 17, 1994). Composition and Product Description of "Gammanorm", four pages.

Pharmacia. (Oct. 17, 1994). Registration Application, Composition and Product Description of "Gammanorm", with English Translation, eight pages.

Physica. Graphic Representation of Viscosity Measurement of Beriglobin®, *Physica*.

Physicians' Desk Reference. (1999). Product Descriptions of Baxter Healthcare products, *Physicians' Desk Reference*, 53rd Edition, Medical Economics Company, Inc., Montvale: NJ, pp: 621-623, 684-690, and 2082-2085.

Pikal et al. (1991) "The Effects of Formulation Variables on the Stability of Freeze-Dried Human Growth Hormone," *Pharmaceutical Research* 8:427-436.

Press Release. (Jun. 19, 2000). "7,500 Pharmaceutical Scientists to Explore Therapies for New Millennium," *AAPS PressRoom*, located at <http://www.aapspharmaceutica.com/about/press/newsrelea . . . >, last visited Apr. 12, 2010, one page.

Presta et al. (Sep. 1, 1993). "Humanization of an Antibody Directed Against IgE," *J. Immunol.* 151(5):2623-2632.

Priority Document, GB0113179.6, of WO 02/096457, dated Aug. 15, 2002.

Reinhart, W.H. et al. (Mar. 14, 1992). "Effect of High-Dose Intravenous Immunoglobulin Therapy on Blood Rheology," *The Lancet* 339:662-664.

Rote Liste®. (1997). Description of "Sera, Immunglobuline u. Impfstoffe," in Rote List®, two pages. (German Language).

Rote Liste®. (1997). Description of "Sera, Immunglobulins and Vaccines," in Rote List®, with English Translation, four pages.

Rote Liste®. (1999_A). Description of "Sera, Immunglobuline u. Impfstoffe," in Rote List®, two pages. (German Language).

Rote Liste®. (1999_A). Description of "Sera, Immunglobulins and Vaccines," in Rote List®, with English Translation, three pages.

Rote Liste®. (1999_B). Description of "Sera, Immunglobuline u. Impfstoffe," in Rote List®, two pages. (German Language).

Rote Liste®. (1999_B). Description of " Sera, Immunglobulins and Vaccines," in Rote List®, with English Translation, three pages.

Rote Liste®. (1999-C). Description of "Sera, Immunglobuline u. Impfstoffe," in Rote List®, two pages. (German Language).

Rote Liste®. (1999_C). Description of " Sera, Immunglobulins and Vaccines," in Rote List®, with English Translation, three pages.

Rote Liste®. (2004). Description of "Sera, Immunglobuline u. Impfstoffe," in Rote List®, two pages. (German Language).

Rote Liste®. (2004). Description of "Sera, Immunglobulins and Vaccines," in Rote List®, with English Translation, four pages.

Saluja, A. et al. (2008). "Nature and Consequences of Protein-Protein Interactions in High Protein Concentration Solutions," *International Journal of Pharmaceutics* 358:1-15.

Sampson, H.A. (2000). "Food Anaphylaxis," *British Medical Bulletin* 56(4):925-935.

Schneider, C. et al. (1990). "Some Viscosity Characteristics of Faba Bean Protein Isolats within a pH Range Relevant for Foods," *Die Nahrung* 34(8):735-745.

Schultz, J.S. et al. (Jan. 1979). "Reflection Coefficients of Homopore Membranes: Effect of Molecular Size and Configuration," *J. Gen. Physiol.* 73:49-60.

Sharma, V.K. et al. (Dec. 30, 2014). "In silico Selection of Therapeutic Antibodies for Development: Viscosity, Clearance, and Chemical Stability," *PNAS* 111(52):18601-18606.

Siegel, F.P. (1990). "Tonicity, Osmoticity, Osmolality and Osmolarity," Chapter 79 in *Remington's Pharmaceutical Sciences*, 18th Edition, Gennaro, A.R. ed., Mack Publishing Company: Easton, PA, pp. 1481-1498.

Simons, F.E.R. (2003). "What's in a Name? The Allergic Rhinitis—Asthma Connection," *Clinical and Experimental Allergy Reviews* 3(1):9-17.

Stokke, B.T. et al. (1981). Human Spectrin. VI. A Viscometric Study, *Biochimica et Biophysica Acta* 640:640-645.

Tanford, C. et al. (1956). "The Viscosity of Aqueous Solutions of Bovine Serum Albumin Between pH 4.3 and 10.5," *J. Phys. Chem.* 60:225-231.

Teschner, W. (Jun. 16, 2010). Technical Expert Declaration, with Exhibits 1-5, 10 pages.

Tian, F. et al. (2006, e-pub. Jan. 19, 2006). "Calorimetric Investigation of Protein/Amino Acid Interactions in the Solid State" *International Journal of Pharmaceutics* 310:175-186.

Tian, F. et al. (2007, e-ub. Oct. 29, 2006). "Spectroscopic Evaluation of the Stabilization of Humanized Monoclonal Antibodies in Amino Acid Formulations" *International Journal of Pharmaceutics* 335:20-31.

Trissel, L.A. (1998). "Immune Globulin Intravenous AHFS 80:04," in *Handbook of Injectable Drugs*, 10th Edition, American Society of Health-System Pharmacists: Bethesda, MD, pp. 676-677.

Tsumoto et al. (Jul. 17-19, 2003). "Magic Agent for Protein Refolding and Solubilization: Arginine," *2003 Colorado Protein Stability Conference*, presented by the University of Colorado Center for the Pharmaceutical Biotechnology, Breckenridge, Colorado.

Van Neerven, R.J. et al. (2001). "Humanized anti-IgE mAb Hu-901 prevents the activation of allergen-specific T cells", *Int Arch. Allergy Immunol.*, 124:400-402.

Vandersande, J. (Jun. 15, 2010). Technical Expert Declaration, with Exhibits 1-7, 20 pages.

Vladutiu, A.O. et al. (1991). "Polyclonal Gammopathy with Marked Increase in Serum Viscosity," *Clin. Chem.* 37(10):1788-1793.

Wagner, J.R. et al. (1992). "Effect of Physical and Chemical Factors on Rheological Behavior of Commercial Soy Protein Isolates: Protein Concentration, Water Imbibing Capacity, Salt Addition, and Thermal Treatment," *J. Agric. Food Chem.* 40:1930-1937.

Wang, N. et al. (Apr. 2009). "Opalescence of an IgG1 Monoclonal Antibody Formulation is Mediated by Ionic Strength and Excipients," *BioPharm International* pp. 36-47.

Wang, W. (1999). "Instability, Stabilization, and Formulation of Liquid Protein Pharmaceuticals," *International Journal of Pharmaceutics* 185:129-188.

Wang, W. et al. (Jan. 2007). "Antibody Structure, Instability, and Formulation," *Journal of Pharmaceutical Sciences* 96(1):1-26.

Wang, Y-C. et al. (1988) "Parentera Formulations of Proteins and Peptides: Stability and Stabilizers," *J. Parenteral Sci. Tech.* (Technical Report No. 10)42(2S):S4-S26.

Warren, J.R. et al. (Aug. 25, 1970). "Denaturation of Globular Proteins: II. The Interaction of Urea with Lysozyme," *The Journal of Biological Chemistry* 245(16):4097-4104.

White et al. (1964). *Principles of Biochemistry*, 3rd Edition, McGraw-Hill Book Company, p. 540.

Wikipedia. (2010). "Reference Ranges for Blood Tests," *Wikipedia, the Free Encyclopedia*, located at <http://en.wikipedia.org.wiki/Reference_ranges_for_blood_tests>, last visited Jun. 3, 2010, 16 pages.

Wikipedia. (2010). Definition of "Viscosity," *Wikipedia, the Free Encyclopedia*, located at <http://en.wikipedia.org.wiki/Viscosity>, last visited Jun. 11, 2010, 56 pages (includes history of revisions).

Xu, X. et al. (1995). "Expression of Functional Insulin-Like Growth Factor-1 Receptor on Lymphoid Cell Subsets of Rats," *Immunology* 85:394-399.

Yardimci, A. (Jun. 15, 2010). Technical Expert Declaration, with Exhibits 1-3, 15 pages.

Yousef, M.A. et al. (1998). "Free-Solvent Model of Osmotic Pressure Revisited: Application to Concentrated IgG Solution under Physiological Conditions," *Journal of Colloid and Interface Science* 197:108-118.

Zietkiewicz et al. (1977). "In Vivo Studies on the Action on the Tissue of the Osmolality of Parenterally Administered Drugs," *Grzyby Drozdzopodobne* (English Translation attached.) 23:869-870.

U.S. Appl. No. 12/197,005, filed Aug. 22, 2008, by Liu et al. (copy not attached.).

(56) References Cited

OTHER PUBLICATIONS

U.S. Appl. No. 13/663,349, filed Oct. 29, 2012, by Esue. (Copy not attached).
U.S. Appl. No. 60/240,107, filed Oct. 12, 2000, by Lui et al.
U.S. Appl. No. 60/293,834, filed May 24, 2001, by Lui et al.
Boulet, L.P. et al. (1997). "Inhibitory Effects of an Anti-IgE Antibody E25 on Allergen-Induced Early Asthmatic Response," *Am J Respir Grit Care Med* 155:1835-1840.
Busse, W. et al. (Jun. 2000). "rhuMAb-E25 (E25), A Novel Therapy for the Treatment of Allergic Asthma (AA)," *Corrected Abstracts: Program and Abstract Papers to Be Presented During Scientific Sessions Aaaai 56$^{th}$ Annual Meeting*, Mar. 3-Mar. 8, 2000, *The Journal of Allergy and Clinical Immunology* 105(6):1245, Abstract No. 5, 3 pages.
Butterweck, H.A. (1972-2005). "Curriclum Vitae," one page.
Cannon Instrument Company. (Apr. 5, 1999). "Certificate of Calibration, Viscometer No. 50, X879," *Cannon Instrument Company*, 1 page.
Cannon Instrument Company. (Oct. 31, 2003). "Report of Test. Analysis of Data ," *Cannon Instrument Company*, 2 pages.
Cannon Instrument Company. (2004). "Instructions for the Use of the Cannon-Fenshke Routine Viscometer," *Cannon Instrument Company*, 1 page.
Casale, T.B. et al. (Jan. 2000). "Relationship Beteen the Clinical Efficacy of rhuMAb-E25 (E25) and Serum Free IgE in Seasonal Allergic Rhinitis," *The Journal of Allergy and Clinical Immunology* 104(1)(Part 2):S356-S357, Abstract No. 1052.
CRC Press. (1992-1993). "Properties of Water in the Range O-100° C.," CRC Handbook of Chemistry and Physics, CRC Press, Boca Raton, FL., Lide, D.R. ed., p. 6-10, (1 page).
De Gruyter, W. (1993). "Hunnius, Pharmazeutisches Worterbuch, Hunnis Pharmecutical Dictionary," Completely reworked and Strongly expanded edition by Artur Burger and Helmut Wachter, Berlin, New York, p. 744, (Geman Only).
Fahey, J.V. et al. (1999). "Effect of Aerosolized Anti-IgE (E25) on Airway Responses to Inhaled Allergen in Asthmatic Subjects," *Am. J. Respir Care Med.* 160:1023-1027.
Manning, R. E. et al. (Jul. 1998). "Glass Capillary Viscometers: Accurate Instruments for Measureing Viscosity," *American Laboratory* 30:6, 8.
Milgrom, H. et al. (Jun. 2000). "The Efficacy and Safety of rhuMAb-E25 (E25) in Children with Allergic Asthma (AA)," *Corrected Abstracts: Program and Abstract Papers to Be Presented During Scientific Sessions Aaaai 56$^{th}$ Annual Meeting*, Mar. 3- Mar. 8, 2000, *The Journal of Allergy and Clinical Immunology* 105(6):1245, Abstract No. 4, 3 Pages.
Rosencranz, R. et al. (2006). "Clinical Laboratory Measurement of Serum, Plasma, and Blood Viscosity," *Am. J. Clin. Pathol.* 125(Suppl. 1):S78-S86.
Sandhagen, B. (1989). "Analysis of Haemorheological Variables—Methodology and Reference Values," *Upsala J. Med. Sci.* 94:81-87.
Supplementary Data. (Jan. 1, 2009). "Annex 2 to Grounds for Appeal: Experiment 5: Temperature and Experimental Feasbility. Annex 3 to Grounds of Appeal: 0125 and use of Different Viscosimeters, European Patent Application No. 01981824.4, Applicant Genentech, Inc.," Genentech, Inc., 1 page.
Warne, N. W. (2011, e-pub. Mar. 13, 2011). "Development of High Concentration Protein Biopharmaceuticals: The Use of Platform Approaches in Formulation Development," *European Journal of Pharmaceutics and Biopharmaceutics* 78:208-212.
U.S. Appl. No. 15/253,689, filed Aug. 31, 2016, for Liu et al. (Copy not attached.).

\* cited by examiner

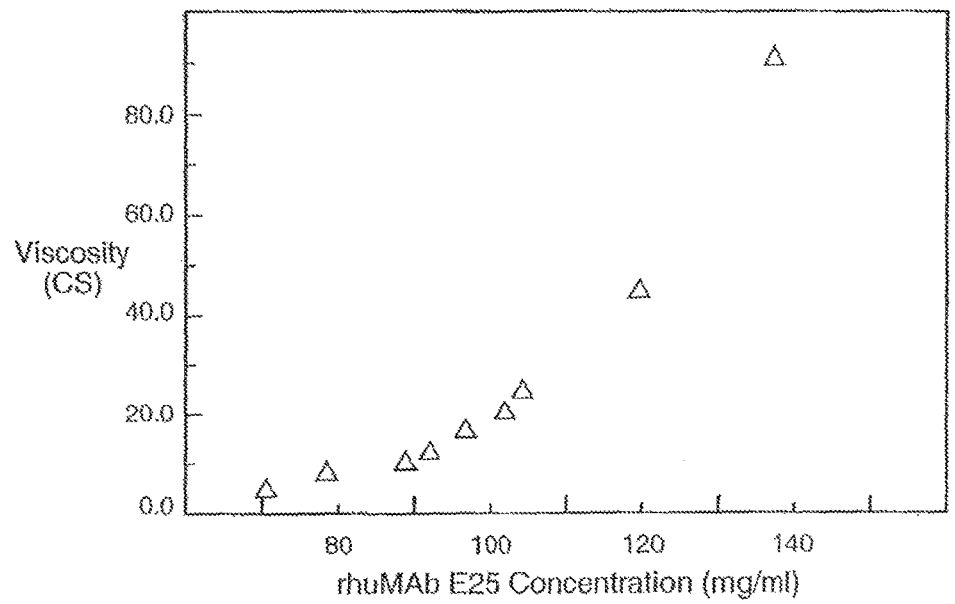
FIG._1
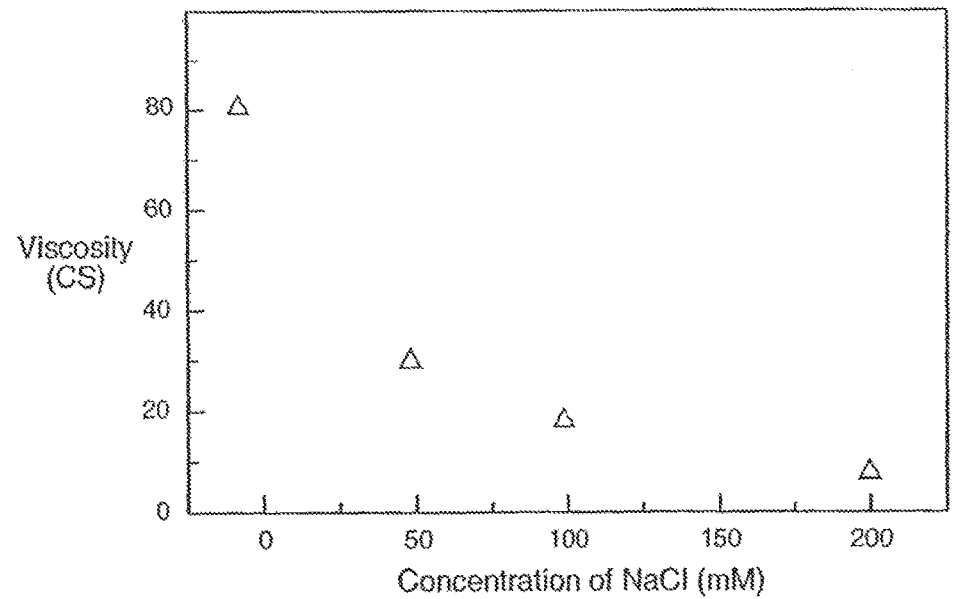
FIG._2

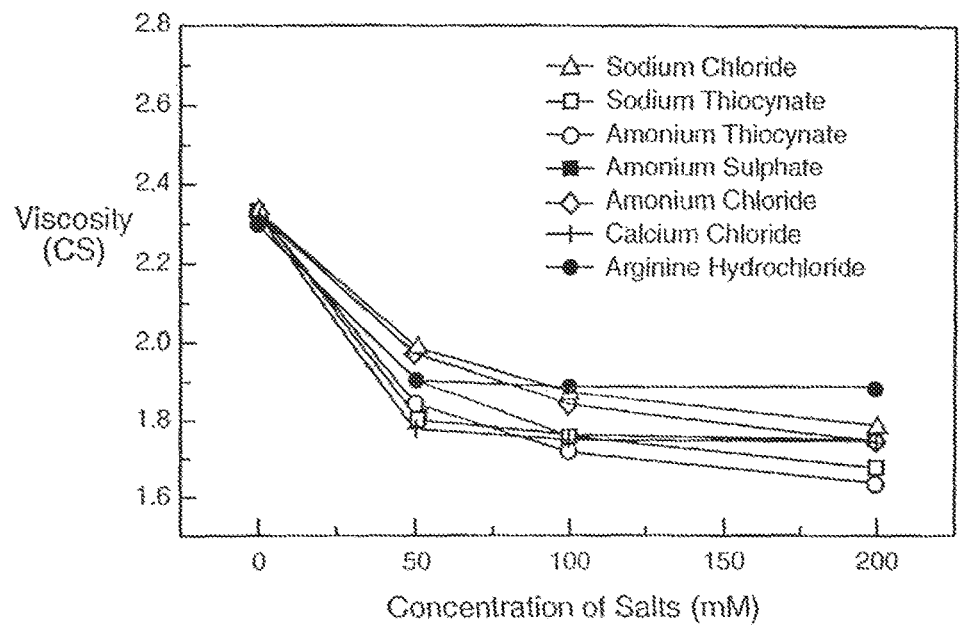
FIG._3
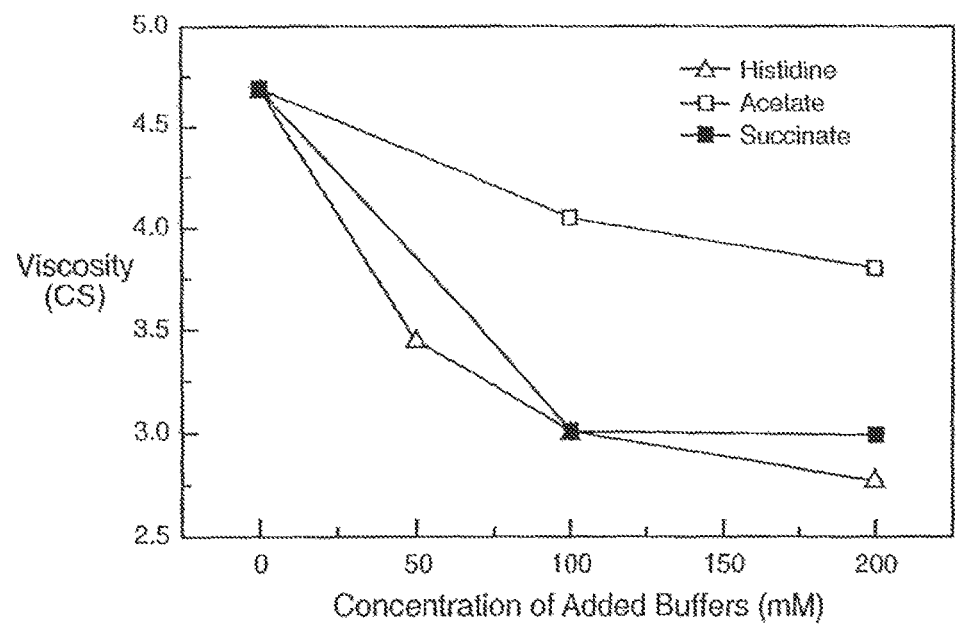
FIG._4

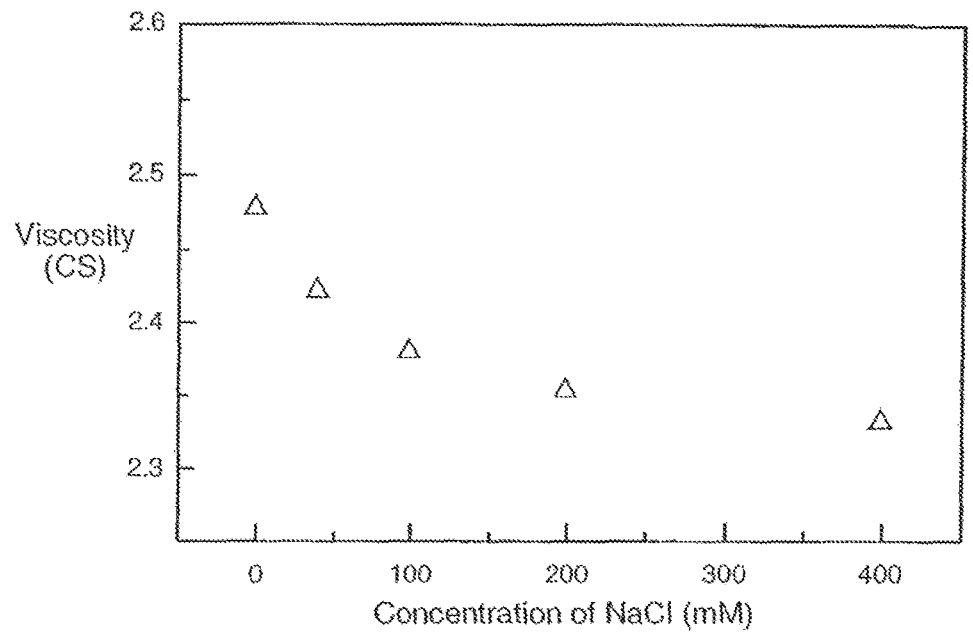
FIG._5
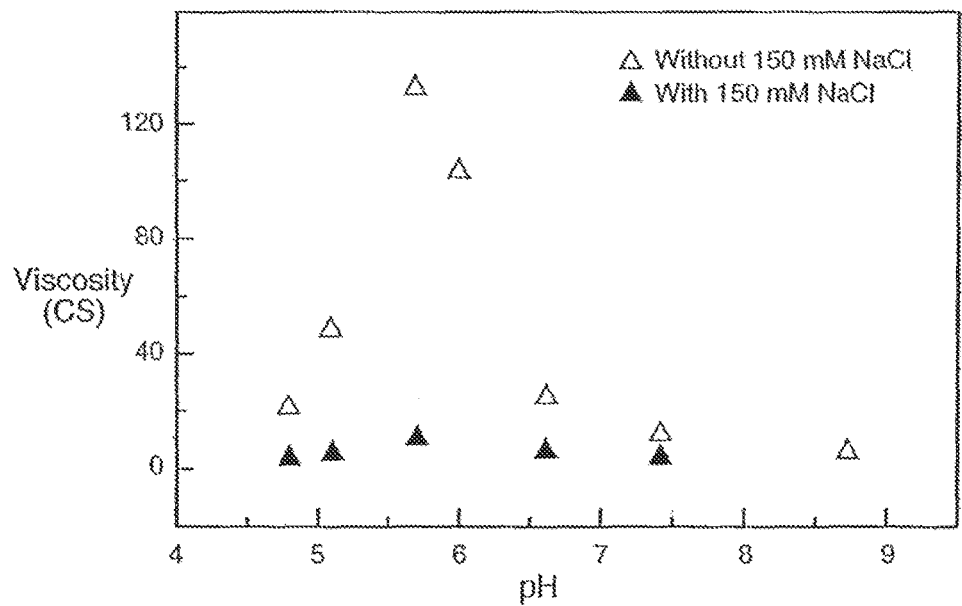
FIG._6

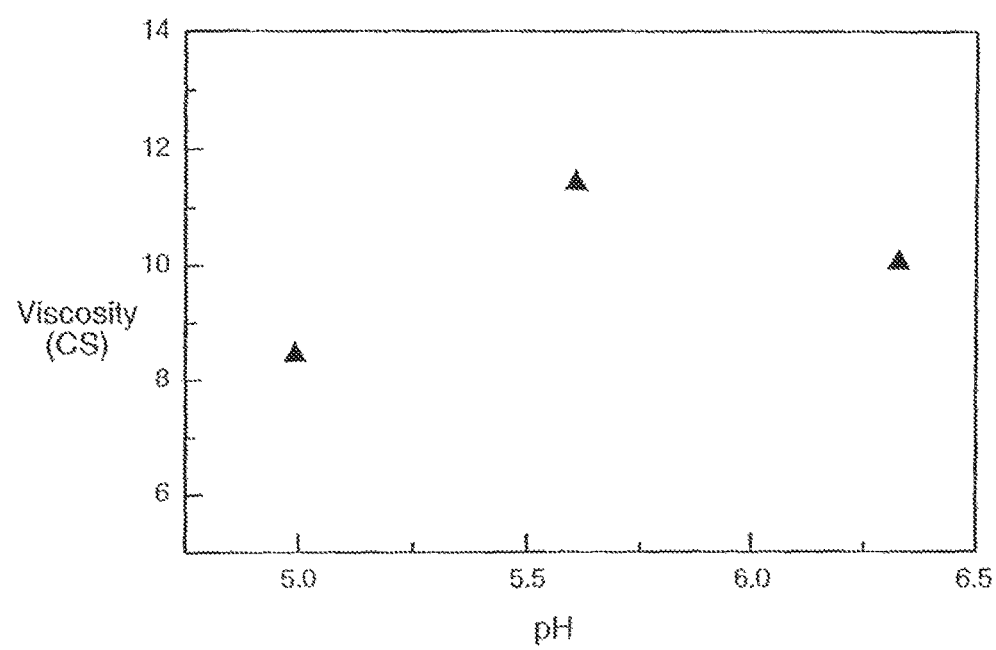
FIG._7

REDUCED-VISCOSITY CONCENTRATED PROTEIN FORMULATIONS

RELATED APPLICATIONS

This application is a continuation of U.S. Ser. No. 13/306,846, filed Nov. 29, 2011, now U.S. Pat. No. 8,703,126, which is a continuation of U.S. Ser. No. 11/611,751, filed Dec. 15, 2006, now U.S. Pat. No. 8,142,776, which is a continuation of U.S. Ser. No. 11/068,553, filed Feb. 28, 2005, now U.S. Pat. No. 7,666,413, which is a divisional of Ser. No. 09/971,511, filed Oct. 4, 2001, now U.S. Pat. No. 6,875,432, which claims the benefit under 35 U.S.C. § 119 of both U.S. Ser. No. 60/293,834, filed May 24, 2001, and U.S. Ser. No. 60/240,107, filed Oct. 12, 2000; the contents all of which are incorporated herein by reference.

BACKGROUND OF THE INVENTION

Field of the Invention

This invention pertains to concentrated protein formulations with reduced viscosity, which are particularly suitable for subcutaneous administration. The invention further concerns a method of reducing viscosity of concentrated protein formulations.

Description of the Related Art

In the past ten years, advances in biotechnology have made it possible to produce a variety of proteins for pharmaceutical applications using recombinant DNA techniques. Because proteins are larger and more complex than traditional organic and inorganic drugs (i.e. possessing multiple functional groups in addition to complex three-dimensional structures), the formulation of such proteins poses special problems. One of the problems is the elevated viscosity values of protein formulations, especially at high concentration. The delivery of high protein concentration is often required for subcutaneous administration due to the volume limitations (≤1.5 ml) and dose requirements (usually ≥50 mg, preferably ≥100 mg). For example, if a protein is to be administered to patients at 2 mg/kg on a weekly basis, the average weekly dose will be 130 mg considering 65 kg as the average weight of patients. Since injection volumes of more than 1.5 ml are not well tolerated for subcutaneous administration, the protein concentration for a weekly subcutaneous administration would have to be approximately 100 mg/ml (130 mg protein in less than 1.5 ml volume). However, highly concentrated protein formulations pose several problems. One problem is the tendency of proteins to form particulates during processing and/or storage, which makes manipulation during further processing difficult. In the case of reconstituted liquid formulations, this is usually circumvented by adding a suitable surfactant (e.g. a polysorbate) during lyophilization or after lyophilization while reconstituting the formulation. Although surfactants have been shown to significantly reduce the degree of particulate formation of proteins, they do not address another problem associated with manipulating and administering concentrated protein formulations. Proteins tend to form viscous solutions at high concentration because of their macromolecular nature and potential for intermolecular interactions. Moreover, many proteins are often lyophilized in the presence of large amounts of lyoprotectants, such as sugar to maintain their stability. The sugar can enhance the intermolecular interactions and increase the viscosity. Highly viscous formulations are difficult to manufacture, draw into a syringe and inject subcutaneously. The use of force in manipulating the viscous formulations leads to excessive frothing, and the resultant detergent-like action of froth has the potential to denature and inactivate the therapeutically active protein. Moreover, viscous solution increases the back-pressure during UF/DF process and makes recovery of protein difficult. This can result in considerable loss of protein product. Satisfactory solution of this problem is lacking in the prior art. Therefore, there is a need to develop a method of reducing the viscosity of a formulation containing high concentration of protein.

Stable isotonic lyophilized protein formulations are disclosed in PCT publication WO 97/04801, published on Feb. 13, 1997, the entire disclosure of which is hereby expressly incorporated by reference. The disclosed lyophilized formulations can be reconstituted to generate high protein-concentration liquid formulations without apparent loss of stability. However, the potential issues associated with the high viscosity of the reconstituted formulations are not addressed.

Applicants have discovered that the preparation of proteinaceous, lyophilized formulation with 100 mM NaCl diluent can result in a slightly hypertonic solution. It had been previously believed that pharmaceutical formulations must be maintained at physiological pH and be isotonic. This belief was based at least in part on the perception that the administration of hypertonic formulation could lead to dehydration and therefore could damage the tissue at the site of injection. However, the belief of the requirement for absolute isotonicity of a pharmaceutical formulation may not be well-founded. For example, Zietkiewicz et al., *Grzyby Drozdzopodobne* 23: 869-870 (1971) have shown that absolute isotonicity of the drugs is not necessary. It was found to be sufficient to avoid the drug solutions that exceed the critical limits of hypertonicity. For example, tissue damage was observed only when hypertonic solution of 1300 mOsmol/Kg (~650 mM NaCl) or higher was administered subcutaneously or intramuscularly to experimental animals. As a result, formulations which are slightly hypertonic, or outside of the physiological pH range do not appear to present a risk of tissue damage at the site of administration.

Applicants have further found that proteinaceous solutions having a lowered (4.0-5.3) or elevated (6.5-12.0) pH was also effective at reducing the viscosity of high concentration protein formulations.

The present invention is directed to providing a high concentration protein formulation with reduced viscosity, which is easy to handle and is suitable for subcutaneous administration. The present invention is further directed to providing a method of reducing viscosity of concentrated protein formulations.

SUMMARY OF THE INVENTION

The present invention concerns a method of lowering the viscosity of concentrated protein composition by: (1) increasing the total ionic strength of the formulation through the addition of salts or buffer components; or (2) altering the pH of the formulation to be lower (≈4.0 to ≈5.3) or elevated (≈6.5 to ≈12.0), without significantly compromising stability or biological activity. Accordingly, the invention concerns methods and means for reducing the viscosity of concentrated protein formulations, primarily to ensure easy manipulation before and during administration to a patient.

In one aspect, the present invention provides a stable formulation of reduced viscosity comprising a protein in an amount of at least about 80 mg/ml and a salt or a buffer in an amount of at least about 50 mM, and having a kinematic viscosity of about 50 cs or less. The salts and/or buffers are pharmaceutically acceptable and are derived from various known acids (inorganic and organic) or base forming metals and amines. Alternatively, the salts and/or buffers may be derived from amino acids. In a specific aspect, the salts are chosen from the group consisting of sodium chloride, arginine hydrochloride, sodium thiocyanate, ammonium thiocyanate, ammonium sulfate, ammonium chloride, calcium chloride, zinc chloride and sodium acetate. In another aspect, the salts or buffers are monovalent. In yet another aspect, the formulation contains the above salt or buffer components in an amount of about 50-200 mM, and has a viscosity of about 2 to 30 cs. In a particular embodiment, the protein in the formulation has a molecular weight of at least about 15-20 kD. In another particular embodiment, the formulation is hypertonic. In yet another particular aspect, the formulation may further comprise a surfactant such as polysorbate. The invention also contemplates a reconstituted formulation that further comprises a lyoprotectant such as sugars. In yet another particular aspect, the lyoprotectant sugar can be, for example, sucrose or trehalose, and may be present in an amount of about 60-300 mM. In another specific aspect, the protein concentration in the reconstituted formulation is about 2-40 times greater than the protein concentration in the mixture before lyophilization.

In another embodiment, the invention provides a stable formulation of reduced viscosity comprising a protein in an amount of at least about 80 mg/ml by having a pH lower ($\approx$4.0 to $\approx$5.3) or elevated ($\approx$6.5 to $\approx$12.0), wherein the kinematic viscosity is reduced to 50 cs or less. In a specific aspect, the viscosity is reduced to about 2 to 30 cs. In another specific aspect, the pH is altered through the addition of a pharmaceutically acceptable acid, base or buffer, and is added in an amount of at least about 10 mM, preferably about 50-200 mM, more preferably about 100-200 mM, most preferably about 150 mM. In a specific aspect, the acid, base and/or buffers are monovalent. In another specific aspect, the acid, base and/or buffers are selected from the group consisting of acetic acid, hydrochloric acid, and arginine. In another particular aspect, the formulation may further comprise a surfactant such as polysorbate. The invention also contemplates a reconstituted formulation that further comprises a lyoprotectant such as sugars. In a particular aspect, the lyoprotectant sugar can be, for example, sucrose or trehalose, and may be present in an amount of about 60-300 mM. In another preferred aspect, the protein concentration in the reconstituted formulation is about 2-40 times greater than the protein concentration in the mixture before lyophilization. In a particular aspect, the pH is any tenth pH value within those enumerated above; for example, for the lower pH value, example values are pH 4.0, 4.1, 4.2, 4.3, 4.4, 4.5, 4.6, 4.7, 4.8, 4.9, 5.0, 5.1, 5.2 and 5.3. At the higher pH range, example values are 6.5, 6.6, 6.7, 6.8, 6.9, 7.0, 7.1, 7.2, 7.3, 7.4, 7.5, 7.6, 7.7, 7.8, 7.9, 8.0, 8.1, 8.2, 8.3, 8.4, 8.5, 8.6, 8.7, 8.8, 8.9, 9.0, 9.1, 9.2, 9.3, 9.4, 9.5, 9.6, 9.7, 9.8, 9.9, 10.0, 10.1, 10.2, 10.3, 10.4, 10.5, 10.6, 10.7, 10.8, 10.9, 11.0, 11.1, 11.2, 11.3, 11.4, 11.5, 11.6, 11.7, 11.8, 11.9 and 12.0.

In a particular embodiment, the invention provides a formulation containing high concentrations of large molecular weight proteins, such as immunoglobulins. The immunoglobulins may, for example, be antibodies directed against a particular predetermined antigen. In a specific aspect, the antigen is IgE (e.g., rhuMAbE-25, rhuMAbE-26 and rhuMAbE-27 described in WO 99/01556). Alternatively, the antigen may include: the CD proteins CD3, CD4, CD8, CD19, CD20 and CD34; members of the HER receptor family such as EGF receptor, HER2, HER3 or HER4 receptor; cell adhesion molecules such as LFA-1, Mo1, p150,95, VLA-4, ICAM-1, VCAM and $\alpha v/\beta 3$ integrin including the $\alpha$- and ($\beta$-subunits thereof (e.g., anti-CD11a, anti-CD18 or anti-CD11b antibodies); growth factors such as VEGF; blood group antigens; flk2/flt3 receptor; obesity (OB) receptor; and protein C.

The formulations of the present invention may be pharmaceutical formulations, in particular, formulations for subcutaneous administration.

In another aspect, the invention provides a method of reducing the viscosity of a formulation containing a protein in an amount of at least about 80 mg/ml by the addition of a salt or buffer component in an amount of at least about 50 mM, wherein the kinematic viscosity is reduced to 50 cs or less. In a specific aspect, the viscosity is reduced to about 2 to 30 cs. In another specific aspect, the salts or buffer components may be added in an amount of at least about 100 mM, preferably about 50-200 mM, more preferably about 100-200 mM, most preferably about 150 mM. The salts and/or buffers are pharmaceutically acceptable and are derived from various known acids (inorganic and organic) with "base forming" metals or amines. Alternatively, the salts and/or buffers may be derived from amino acids. In yet another specific aspect, the salts and/or buffers are monovalent. In yet another specific aspect, the salts are selected from the group consisting of sodium chloride, arginine hydrochloride, sodium thiocyanate, ammonium thiocyanate, ammonium sulfate, ammonium chloride, calcium chloride, zinc chloride and sodium acetate. In yet another aspect, the formulation contains the above salt or buffer components in an amount of about 50-200 mM, and has a viscosity of about 2 to 30 cs. In yet another aspect, the protein in the formulation has a molecular weight of at least about 15-20 kD. In another particular embodiment, the formulation may further comprise a surfactant such as polysorbate. The invention also contemplates a reconstituted formulation that further comprises a lyoprotectant such a sugar. In a particular aspect, the lyoprotectant sugar can be, for example, sucrose or trehalose, and may be present in an amount of about 60-300 mM. In a specific aspect, the formulation can be reconstituted with a diluent comprising the buffer or salt. In a preferred embodiment, the protein concentration in the reconstituted formulation is about 2-40 times greater than the protein concentration in the mixture before lyophilization.

In yet another embodiment, the invention provides a method for reducing the viscosity comprising a protein in an amount of at least about 80 mg/ml by altering the pH to be lower ($\approx$4.0 to $\approx$5.3) or elevated to ($\approx$6.5 to $\approx$12.0), wherein the kinematic viscosity is reduced to 50 cs or less. In a specific aspect, the viscosity is reduced to about 2 to 30 cs. In another specific aspect, the pH is altered through the addition of a pharmaceutically acceptable acid, base or buffer, and is added in an amount of at least about 10 mM, preferably about 50-200 mM, more preferably about 100-200 mM, most preferably about 150 mM. In a specific aspect, the acid, base and/or buffers are monovalent. In an another specific aspect, the acid, base and/or buffers are selected from the group consisting of acetic acid, hydrochloric acid, and arginine. In another particular embodiment, the formulation may further comprise a surfactant such as polysorbate. The invention also contemplates a reconstituted formulation that further comprises a lyoprotectant such as sugars. In a particular aspect, the lyoprotectant sugar can be, for example, sucrose or trehalose, and may be present in an amount of about 60-300 mM. In a preferred embodiment, the protein concentration in the reconstituted formulation is about 2-40 times greater than the protein concentration in the mixture before lyophilization. In a particular aspect, the pH is any tenth pH value within those enumerated above; for example, for the lower pH value, example values are pH 4.0, 4.1, 4.2, 4.3, 4.4, 4.5, 4.6, 4.7, 4.8, 4.9, 5.0, 5.1, 5.2 and 5.3. At the higher pH range, example values are 6.5, 6.6, 6.7, 6.8, 6.9, 7.0, 7.1, 7.2, 7.3, 7.4, 7.5, 7.6, 7.7, 7.8, 7.9, 8.0, 8.1, 8.2, 8.3, 8.4, 8.5, 8.6, 8.7, 8.8, 8.9, 9.0, 9.1, 9.2, 9.3, 9.4, 9.5, 9.6, 9.7, 9.8, 9.9, 10.0, 10.1, 10.2, 10.3, 10.4, 10.5, 10.6, 10.7, 10.8, 10.9, 11.0, 11.1, 11.2, 11.3, 11.4, 11.5, 11.6, 11.7, 11.8, 11.9 and 12.0.

In yet another aspect, the invention provides a method of reducing the viscosity of a formulation of a protein having a molecular weight of at least about 15-20 kD, including immunoglobulins, specifically antibodies which specifically bind to a particular antigen. In a specific aspect, the method is used to prepare a reconstitutable formulation, especially those that are concentrated to a much greater concentration of therapeutic protein (e.g., 2-40 times) after the concentration step (e.g., lyophilization) compared to before.

In yet another embodiment, the invention provides a method for the treatment, prophylactic or therapeutic, of a disorder treatable by the protein (e.g. antibody) formulated, using the formulations disclosed herein. Such formulations are particularly useful for subcutaneous administration.

Also provided is an article of manufacture comprising a container enclosing a formulation disclosed herein.

In yet another embodiment, the present invention discloses a method of preventing self-association of proteins in concentrated liquid formulations by (1) adding a salt or a buffer component in an amount of at least about 50 mM; or (2) altering the pH by lowering to ($\approx$4.0 to $\approx$5.3) or elevating to ($\approx$6.5 to $\approx$12.0). In a specific aspect, the self-association to be prevented is that induced or exacerbated by the presence of sugars (e.g., sucrose or trehalose) that are commonly used as lyoprotectants. Accordingly, this method is particularly useful for preventing self-association of reconstituted lyophilized formulations.

BRIEF DESCRIPTION OF THE DRAWINGS

FIG. 1 shows the effects of protein concentration on viscosity of reconstituted formulation containing the anti-IgE antibody rhuMAb E25, 16 mM histidine, 266 mM sucrose and 0.03% Polysorbate 20 at 25° C.

FIG. 2 depicts the effects of NaCl concentration on viscosity of reconstituted formulation containing 125 mg/ml of the antibody IgE antibody rhuMAb E25, 16 mM histidine, 266 mM sucrose, 0.03% Polysorbate 20 and various amounts of NaCl at 25° C.

FIG. 3 shows the effects of various salts on viscosity of reconstituted formulation containing 40 mg/ml of the anti-IgE antibody rhuMAb E25, 10 mM histidine, 250 mM sucrose, 0.01% Polysorbate 20 and various amounts of salts at 25° C.

FIG. 4 shows the effects of buffer concentration on viscosity of a liquid formulation containing 80 mg/ml of the anti-IgE antibody rhuMAb E25, 50 mM histidine, 150 mM trehalose, 0.05% Polysorbate 20 and various amounts of histidine, acetate, or succinate components at 25° C.

FIG. 5 shows the effects of NaCl concentration on viscosity of a reconstituted formulation containing 21 mg/ml rhuMAb E26, 5 mM histidine, 275 mM sucrose at 6° C.

FIG. 6 shows the effects of pH on viscosity of liquid formulations containing 130 mg/ml rhuMAb E25, 2-17.5 mM of acetate or arginine with and without 150 mM NaCl at 25° C.

FIG. 7 shows the effects of pH on viscosity of reconstituted lyophilized formulations containing 94 mg/ml rhuMAb E25, 250 mM trehalose, 20 mM histidine, at 25° C.

DETAILED DESCRIPTION OF THE PREFERRED EMBODIMENT

I. Definitions

By "protein" is meant a sequence of amino acids for which the chain length is sufficient to produce the higher levels of tertiary and/or quaternary structure. Thus, proteins are distinguished from "peptides" which are also amino acid-based molecules that do not have such structure. Typically, a protein for use herein will have a molecular weight of at least about 15-20 kD, preferably at least about 20 kD.

Examples of proteins encompassed within the definition herein include mammalian proteins, such as, e.g., growth hormone, including human growth hormone and bovine growth hormone; growth hormone releasing factor; parathyroid hormone; thyroid stimulating hormone; lipoproteins; $\alpha$-1-antitrypsin; insulin A-chain; insulin B-chain; proinsulin; follicle stimulating hormone; calcitonin; luteinizing hormone; glucagon; clotting factors such as factor VIIIC, factor IX, tissue factor, and von Willebrands factor; anti-clotting factors such as Protein C; atrial natriuretic factor; lung surfactant; a plasminogen activator, such as urokinase or tissue-type plasminogen activator (t-PA, e.g., Activase®, TNKase®, Retevase®); bombazine; thrombin; tumor necrosis factor-$\alpha$ and -$\beta$; enkephalinase; RANTES (regulated on activation normally T-cell expressed and secreted); human macrophage inflammatory protein (MIP-1-$\alpha$); serum albumin such as human scrum albumin; mullerian-inhibiting substance; relaxin A-chain; relaxin B-chain; prorelaxin; mouse gonadotropin-associated peptide; DNase; inhibin; activin; vascular endothelial growth factor (VEGF); receptors for hormones or growth factors; an integrin; protein A or D; rheumatoid factors; a neurotrophic factor such as bone-derived neurotrophic factor (BDNF), neurotrophin-3, -4, -5, or -6 (NT-3, NT-4, NT-5, or NT-6), or a nerve growth factor such as NGF-$\beta$; platelet-derived growth factor (PDGF); fibroblast growth factor such as aFGF and bFGF; epidermal growth factor (EGF); transforming growth factor (TGF) such as TGF-$\alpha$ and TGF-$\beta$, including TGF-$\beta$1, TGF-$\beta$2, TGF-$\beta$3, TGF-$\beta$4, or TGF-$\beta$5; insulin-like growth factor-I and -II (IGF-I and IGF-II); des(1-3)-IGF-I (brain IGF-I); insulin-like growth factor binding proteins; CD proteins such as CD3, CD4, CD8, CD19 and CD20; erythropoietin (EPO); thrombopoietin (TPO); osteoinductive factors; immunotoxins; a bone morphogenetic protein (BMP); an interferon such as interferon-$\alpha$, -$\beta$, and -$\gamma$; colony stimulating factors (CSFs), e.g., M-CSF, GM-CSF, and G-CSF; interleukins (ILs), e.g., IL-1 to IL-10; superoxide dismutase; T-cell receptors; surface membrane proteins; decay accelerating factor (DAF); a viral antigen such as, for example, a portion of the AIDS envelope; transport proteins; homing receptors; addressins; regulatory proteins; immunoadhesins; antibodies; and biologically active fragments or variants of any of the above-listed polypeptides.

The protein which is formulated is preferably essentially pure and desirably essentially homogeneous (i.e. free from contaminating proteins). "Essentially pure" protein means a composition comprising at least about 90% by weight of the protein, based on total weight of the composition, preferably at least about 95% by weight. "Essentially homogeneous"

protein means a composition comprising at least about 99% by weight of protein, based on total weight of the composition.

In certain embodiments, the protein is an antibody. The antibody may bind to any of the above-mentioned molecules, for example. Exemplary molecular targets for antibodies encompassed by the present invention include CD proteins such as CD3, CD4, CD8, CD19, CD20 and CD34; members of the HER receptor family such as the EGF receptor, HER2, HER3 or HER4 receptor; cell adhesion molecules such as LFA-1, Mo1, p150,95, VLA-4, ICAM-1, VCAM and αv/β3 integrin including either α or β subunits thereof (e.g. anti-CD11a, anti-CD18 or anti-CD11b antibodies); growth factors such as VEGF; IgE; blood group antigens; flk2/flt3 receptor; obesity (OB) receptor; protein C etc.

The term "antibody" is used in the broadest sense and specifically covers monoclonal antibodies (including full length antibodies which have an immunoglobulin Fc region), antibody compositions with polyepitopic specificity, bispecific antibodies, diabodies, and single-chain molecules, as well as antibody fragments (e.g., Fab, F(ab')$_2$, and Fv).

The basic 4-chain antibody unit is a heterotetrameric glycoprotein composed of two identical light (L) chains and two identical heavy (H) chains. An IgM antibody consists of 5 of the basic heterotetramer unit along with an additional polypeptide called a J chain, and contains 10 antigen binding sites, while IgA antibodies comprise from 2-5 of the basic 4-chain units which can polymerize to form polyvalent assemblages in combination with the J chain. In the case of IgGs, the 4-chain unit is generally about 150,000 daltons. Each L chain is linked to an H chain by one covalent disulfide bond, while the two H chains are linked to each other by one or more disulfide bonds depending on the H chain isotype. Each H and L chain also has regularly spaced intrachain disulfide bridges. Each H chain has at the N-terminus, a variable domain ($V_H$) followed by three constant domains ($C_H$) for each of the α and γ chains and four $C_H$ domains for μ and ε isotypes. Each L chain has at the N-terminus, a variable domain ($V_L$) followed by a constant domain at its other end. The $V_L$ is aligned with the $V_H$ and the $C_L$ is aligned with the first constant domain of the heavy chain ($C_H1$). Particular amino acid residues are believed to form an interface between the light chain and heavy chain variable domains. The pairing of a $V_H$ and $V_L$ together forms a single antigen-binding site. For the structure and properties of the different classes of antibodies, see e.g., *Basic and Clinical Immunology*, 8th Edition, Daniel P. Sties, Abba I. Terr and Tristram G. Parsolw (eds), Appleton & Lange, Norwalk, Conn., 1994, page 71 and Chapter 6.

The L chain from any vertebrate species can be assigned to one of two clearly distinct types, called kappa and lambda, based on the amino acid sequences of their constant domains. Depending on the amino acid sequence of the constant domain of their heavy chains (CH), immunoglobulins can be assigned to different classes or isotypes. There are five classes of immunoglobulins: IgA, IgD, IgE, IgG and IgM, having heavy chains designated α, δ, ε, γ and μ, respectively. The γ and μ classes are further divided into subclasses on the basis of relatively minor differences in the CH sequence and function, e.g., humans express the following subclasses: IgG1, IgG2, IgG3, IgG4, IgA1 and IgA2.

The term "variable" refers to the fact that certain segments of the variable domains differ extensively in sequence among antibodies. The V domain mediates antigen binding and defines the specificity of a particular antibody for its particular antigen. However, the variability is not evenly distributed across the entire span of the variable domains. Instead, the V regions consist of relatively invariant stretches called framework regions (FRs) of about 15-30 amino acid residues separated by shorter regions of extreme variability called "hypervariable regions" or sometimes "complementarity determining regions" (CDRs) that are each approximately 9-12 amino acid residues in length. The variable domains of native heavy and light chains each comprise four FRs, largely adopting a β-sheet configuration, connected by three hypervariable regions, which form loops connecting, and in some cases forming part of, the β-sheet structure. The hypervariable regions in each chain are held together in close proximity by the FRs and, with the hypervariable regions from the other chain, contribute to the formation of the antigen binding site of antibodies (see Kabat et al., *Sequences of Proteins of Immunological Interest*, 5th Ed. Public Health Service, National Institutes of Health, Bethesda, Md. (1991). The constant domains are not involved directly in binding an antibody to an antigen, but exhibit various effector functions, such as participation of the antibody dependent cellular cytotoxicity (ADCC).

The term "hypervariable region" (also known as "complementarity determining regions" or CDRs) when used herein refers to the amino acid residues of an antibody which are (usually three or four short regions of extreme sequence variability) within the V-region domain of an immunoglobulin which form the antigen-binding site and are the main determinants of antigen specificity. There are at least two methods for identifying the CDR residues: (1) An approach based on cross-species sequence variability (i.e., Kabat et al., *Sequences of Proteins of Immunological Interest* (National Institute of Health, Bethesda, Md. 1991); and (2) An approach based on crystallographic studies of antigen-antibody complexes (Chothia, C. et al., *J. Mol. Biol.* 196: 901-917 (1987)). However, to the extent that two residue identification techniques define regions of overlapping, but not identical regions, they can be combined to define a hybrid CDR.

The term "monoclonal antibody" as used herein refers to an antibody obtained from a population of substantially homogeneous antibodies, i.e., the individual antibodies comprising the population are identical except for possible naturally occurring mutations that may be present in minor amounts. Monoclonal antibodies are highly specific, being directed against a single antigenic site. Furthermore, in contrast to conventional (polyclonal) antibody preparations which typically include different antibodies directed against different determinants (epitopes), each monoclonal antibody is directed against a single determinant on the antigen. In addition to their specificity, the monoclonal antibodies are advantageous in that they are synthesized by the hybridoma culture, uncontaminated by other immunoglobulins. The modifier "monoclonal" indicates the character of the antibody as being obtained from a substantially homogeneous population of antibodies, and is not to be construed as requiring production of the antibody by any particular method. For example, the monoclonal antibodies to be used in accordance with the present invention may be made by the hybridoma method first described by Kohler et al., *Nature*, 256: 495 (1975), or may be made by recombinant DNA methods (see, e.g., U.S. Pat. No. 4,816,567). The "monoclonal antibodies" may also be isolated from phage antibody libraries using the techniques described in Clackson et al., *Nature*, 352:624-628 (1991) and Marks et al., *J. Mol. Biol.*, 222:581-597 (1991), for example.

The monoclonal antibodies herein specifically include "chimeric" antibodies (immunoglobulins) in which a portion of the heavy and/or light chain is identical with or homologous to corresponding sequences in antibodies derived from a particular species or belonging to a particular antibody class or subclass, while the remainder of the chain(s) is(are) identical with or homologous to corresponding sequences in antibodies derived from another species or belonging to another antibody class or subclass, as well as fragments of such antibodies, so long as they exhibit the desired biological activity (U.S. Pat. No. 4,816,567; Morrison et al., *Proc. Natl. Acad. Sci. USA*, 81:6851-6855 (1984)).

An "intact" antibody is one which comprises an antigen-binding site as well as a CL and at least the heavy chain domains, $C_H1$, $C_H2$ and $C_H3$.

An "antibody fragment" comprises a portion of an intact antibody, preferably the antigen binding and/or the variable region of the intact antibody. Examples of antibody fragments include Fab, Fab', F(ab')$_2$ and Fv fragments; diabodies; linear antibodies (see U.S. Pat. No. 5,641,870, Example 2; Zapata et al., *Protein Eng*. 8(10): 1057-1062 [1995]); single-chain antibody molecules and multispecific antibodies formed from antibody fragments.

Papain digestion of antibodies produced two identical antigen-binding fragments, called "Fab" fragments, and a residual "Fc" fragment, a designation reflecting the ability to crystallize readily. The Fab fragment consists of an entire L chain along with the variable region domain of the H chain ($V_H$), and the first constant domain of one heavy chain ($C_H1$). Each Fab fragment is monovalent with respect to antigen binding, i.e., it has a single antigen-binding site. Pepsin treatment of an antibody yields a single large F(ab')$_2$ fragment which roughly corresponds to two disulfide linked Fab fragments having different antigen-binding activity and is still capable of cross-linking antigen. Fab' fragments differ from Fab fragments by having a few additional residues at the carboxy terminus of the $C_H1$ domain including one or more cysteines from the antibody hinge region. Fab'-SH is the designation herein for Fab' in which the cysteine residue (s) of the constant domains bear a free thiol group. F(ab')$_2$ antibody fragments originally were produced as pairs of Fab' fragments which have hinge cysteines between them. Other chemical couplings of antibody fragments are also known.

The Fc fragment comprises the carboxy-terminal portions of both H chains held together by disulfides. The effector functions of antibodies are determined by sequences in the Fc region, the region which is also recognized by Fc receptors (FcR) found on certain types of cells.

"Fv" is the minimum antibody fragment which contains a complete antigen-recognition and -binding site. This fragment consists of a dimer of one heavy- and one light-chain variable region domain in tight, non-covalent association. From the folding of these two domains emanate six hypervariable loops (3 loops each from the H and L chain) that contribute the amino acid residues for antigen binding and confer antigen binding specificity to the antibody. However, even a single variable domain (or half of an Fv comprising only three CDRs specific for an antigen) has the ability to recognize and bind antigen, although at a lower affinity than the entire binding site.

"Single-chain Fv" also abbreviated as "sFv" or "scFv" are antibody fragments that comprise the VH and VL antibody domains connected into a single polypeptide chain. Preferably, the sFv polypeptide further comprises a polypeptide linker between the $V_H$ and $V_L$ domains which enables the sFv to form the desired structure for antigen binding. For a review of the sFv, see Pluckthun in *The Pharmacology of Monoclonal Antibodies*, vol. 113, Rosenburg and Moore eds., Springer-Verlag, New York, pp. 269-315 (1994).

The term "diabodies" refers to small antibody fragments prepared by constructing sFv fragments (see preceding paragraph) with short linkers (about 5-10) residues) between the $V_H$ and $V_L$ domains such that inter-chain but not intra-chain pairing of the V domains is achieved, thereby resulting in a bivalent fragment, i.e., a fragment having two antigen-binding sites. Bispecific diabodies are heterodimers of two "crossover" sFv fragments in which the $V_H$ and $V_L$ domains of the two antibodies are present on different polypeptide chains. Diabodies are described in greater detail in, for example, EP 404,097; WO 93/11161; Hollinger et al., *Proc. Natl. Acad. Sci. USA* 90: 6444-6448 (1993).

An antibody that "specifically binds to" or is "specific for" a particular polypeptide or an epitope on a particular polypeptide is one that binds to that particular polypeptide or epitope on a particular polypeptide without substantially binding to any other polypeptide or polypeptide epitope.

"Humanized" forms of non-human (e.g., murine) antibodies are chimeric immunoglobulins, immunoglobulin chains or fragments thereof (such as Fv, Fab, Fab', F(ab')$_2$ or other antigen-binding subsequences of antibodies) of mostly human sequences, which contain minimal sequence derived from non-human immunoglobulin. For the most part, humanized antibodies are human immunoglobulins (recipient antibody) in which residues from a hypervariable region (also CDR) of the recipient are replaced by residues from a hypervariable region of a non-human species (donor antibody) such as mouse, rat or rabbit having the desired specificity, affinity, and capacity. In some instances, Fv framework region (FR) residues of the human immunoglobulin are replaced by corresponding non-human residues. Furthermore, "humanized antibodies" as used herein may also comprise residues which are found neither in the recipient antibody nor the donor antibody. These modifications are made to further refine and optimize antibody performance. The humanized antibody optimally also will comprise at least a portion of an immunoglobulin constant region (Fc), typically that of a human immunoglobulin. For further details, see Jones et al., *Nature*, 321:522-525 (1986); Reichmann et al., *Nature*, 332:323-329 (1988); and Presta, *Curr. Op. Struct. Biol.*, 2:593-596 (1992).

Antibody "effector functions" refer to those biological activities attributable to the Fc region (a native sequence Fc region or amino acid sequence variant Fc region) of an antibody, and vary with the antibody isotype. Examples of antibody effector functions include: C1q binding and complement dependent cytotoxicity; Fc receptor binding; antibody-dependent cell-mediated cytotoxicity (ADCC); phagocytosis; down regulation of cell surface receptors (e.g., B cell receptors); and B cell activation.

"Antibody-dependent cell-mediated cytotoxicity" or ADCC refers to a form of cytotoxicity in which secreted Ig bound onto Fc receptors (FcRs) present on certain cytotoxic cells (e.g., natural killer (NK) cells, neutrophils and macrophages) enable these cytotoxic effector cells to bind specifically to an antigen-bearing target cell and subsequently kill the target cell with cytotoxins. The antibodies "arm" the cytotoxic cells and are required for killing of the target cell by this mechanism. The primary cells for mediating ADCC, NK cells, express FcγRIII only, whereas monocytes express FcγRI, FcγRII and FcγRIII. Fc expression on hematopoietic cells is summarized in Table 3 on page 464 of Ravetch and Kinet, *Annu. Rev. Immunol.* 9: 457-92 (1991). To assess ADCC activity of a molecule of interest, an in vitro ACDD assay, such as that described in U.S. Pat. No. 5,500,362 or 5,821,337 may be performed. Useful effector cells for such assays include peripheral blood mononuclear cells (PBMC)

and natural killer (NK) cells. Alternatively, or additionally, ADCC activity of the molecule of interest may be assessed in vivo, e.g., in an animal model such as that disclosed in Clynes et al., *PNAS USA* 95:652-656 (1998).

"Fc receptor" or "FcR" describes a receptor that binds to the Fc region of an antibody. The preferred FcR is a native sequence human FcR. Moreover, a preferred FcR is one which binds an IgG antibody (a gamma receptor) and includes receptors of the FcγRI, FcγRII, and FcγRIII subclasses, including allelic variants and alternatively spliced forms of these receptors, FcγRII receptors include FcγRIIA (an "activating receptor") and FcγRIIB (an "inhibiting receptor"), which have similar amino acid sequences that differ primarily in the cytoplasmic domains thereof. Activating receptor FcγRIIA contains an immunoreceptor tyrosine-based activation motif (ITAM) in its cytoplasmic domain. Inhibiting receptor FcγRIIB contains an immunoreceptor tyrosine-based inhibition motif (ITIM) in its cytoplasmic domain. (see M. Daëron, *Annu. Rev. Immunol.* 15:203-234 (1997). FcRs are reviewed in Ravetch and Kinet, *Annu. Rev. Immunol.* 9: 457-92 (1991); Capel et al., *Immunomethods* 4: 25-34 (1994); and de Haas et al., *J. Lab. Clin. Med.* 126: 330-41 (1995). Other FcRs, including those to be identified in the future, are encompassed by the term "FcR" herein. The term also includes the neonatal receptor, FcRn, which is responsible for the transfer of maternal IgGs to the fetus. Guyer et al., *J. Immunol.* 117: 587 (1976) and Kim et al., *J. Immunol.* 24: 249 (1994).

"Human effector cells" are leukocytes which express one or more FcRs and perform effector functions. Preferably, the cells express at least FcγRIII and perform ADCC effector function. Examples of human leukocytes which mediate ADCC include peripheral blood mononuclear cells (PBMC), natural killer (NK) cells, monocytes, cytotoxic T cells and neutrophils, with PBMCs and MNK cells being preferred. The effector cells may be isolated from a native source, e.g., blood.

"Complement dependent cytotoxicity" of "CDC" refers to the lysis of a target cell in the presence of complement. Activation of the classical complement pathway is initiated by the binding of the first component of the complement system (C1q) to antibodies (of the appropriate subclass) which are bound to their cognate antigen. To assess complement activation, a CDC assay, e.g., as described in Gazzano-Santoro et al., *J. Immunol. Methods* 202: 163 (1996), may be performed.

A "stable" formulation is one in which the protein therein essentially retains its physical and chemical stability and integrity upon storage. Various analytical techniques for measuring protein stability are available in the art and are reviewed in *Peptide and Protein Drug Delivery*, 247-301, Vincent Lee Ed., Marcel Dekker, Inc., New York, N.Y., Pubs. (1991) and Jones, A. *Adv. Drug Delivery Rev.* 10: 29-90 (1993). Stability can be measured at a selected temperature for a selected time period. For rapid screening, the formulation may be kept at 40° C. for 2 weeks to 1 month, at which time stability is measured. Where the formulation is to be stored at 2-8° C., generally the formulation should be stable at 30° C. or 40° C. for at least 1 month and/or stable at 2-8° C. for at least 2 years. Where the formulation is to be stored at 30° C., generally the formulation should be stable for at least 2 years at 30° C. and/or stable at 40° C. for at least 6 months. For example, the extent of aggregation following lyophilization and storage can be used as an indicator of protein stability. Thus, a "stable" formulation may be one wherein less than about 10% and preferably less than about 5% of the protein are present as an aggregate in the formulation. In other embodiments, any increase in aggregate formation following lyophilization and storage of the lyophilized formulation can be determined. For example, a "stable" lyophilized formulation may be one wherein the increase in aggregate in the lyophilized formulation is less than about 5% and preferably less than about 3%, when the lyophilized formulation is stored at 2-8° C. for at least one year. In other embodiments, stability of the protein formulation may be measured using a biological activity assay.

A "reconstituted" formulation is one which has been prepared by dissolving a lyophilized protein formulation in a diluent such that the protein is dispersed in the reconstituted formulation. The reconstituted formulation is suitable for administration (e.g. parenteral administration) to a patient to be treated with the protein of interest and, in certain embodiments of the invention, may be one which is suitable for subcutaneous administration.

An "isotonic" formulation is one which has essentially the same osmotic pressure as human blood. Isotonic formulations will generally have an osmotic pressure from about 250 to 350 mOsm. The term "hypotonic" describes a formulation with an osmotic pressure below that of human blood. Correspondingly, the term "hypertonic" is used to describe a formulation with an osmotic pressure above that of human blood. Isotonicity can be measured using a vapor pressure or ice-freezing type osmometer, for example. The formulations of the present invention are hypertonic as a result of the addition of salt and/or buffer.

A "pharmaceutically acceptable acid" includes inorganic and organic acids which are non toxic at the concentration and manner in which they are formulated. For example, suitable inorganic acids include hydrochloric, perchloric, hydrobromic, hydroiodic, nitric, sulfuric, sulfonic, sulfinic, sulfanilic, phosphoric, carbonic, etc. Suitable organic acids include straight and branched-chain alkyl, aromatic, cyclic, cyloaliphatic, arylaliphatic, heterocyclic, saturated, unsaturated, mono, di- and tri-carboxylic, including for example, formic, acetic, 2-hydroxyacetic, trifluoroacetic, phenylacetic, trimethylacetic, t-butyl acetic, anthranilic, propanoic, 2-hydroxypropanoic, 2-oxopropanoic, propandioic, cyclopentanepropionic, cyclopentane propionic, 3-phenylpropionic, butanoic, butandioic, benzoic, 3-(4-hydroxybenzoyl)benzoic, 2-acetoxy-benzoic, ascorbic, cinnamic, lauryl sulfuric, stearic, muconic, mandelic, succinic, embonic, fumaric, malic, maleic, hydroxymaleic, malonic, lactic, citric, tartaric, glycolic, glyconic, gluconic, pyruvic, glyoxalic, oxalic, mesylic, succinic, salicylic, phthalic, palmoic, palmeic, thiocyanic, methanesulphonic, ethanesulphonic, 1,2-ethanedisulfonic, 2-hydroxyethanesulfonic, benzenesulphonic, 4-chorobenzenesulfonic, napthalene-2-sulphonic, p-toluenesulphonic, camphorsulphonic, 4-methylbicyclo [2.2.2]-oct-2-ene-1-carboxylic, glucoheptonic, 4,4'-methylenebis-3-(hydroxy-2-ene-1-carboxylic acid), hydroxynapthoic.

"Pharmaceutically-acceptable bases" include inorganic and organic bases were are non-toxic at the concentration and manner in which they are formulated. For example, suitable bases include those formed from inorganic base forming metals such as lithium, sodium, potassium, magnesium, calcium, ammonium, iron, zinc, copper, manganese, aluminum, N-methylglucamine, morpholine, piperidine and organic nontoxic bases including, primary, secondary and tertiary amine, substituted amines, cyclic amines and basic ion exchange resins, [e.g., $N(R')_4^+$ (where R' is independently H or $C_{1-4}$ alkyl, e.g., ammonium, Tris)], for example, isopropylamine, trimethylamine, diethylamine, triethylamine, tripropylamine, ethanolamine, 2-diethylaminoethanol, trimethamine, dicyclohexylamine, lysine, arginine, histidine, caffeine, procaine, hydrabamine, choline, betaine, ethylenediamine, glucosamine, methylglucamine, theobromine, purines, piperazine, piperidine, N-ethylpiperidine, polyamine resins and the like. Particularly preferred organic non-toxic bases are isopropylamine, diethylamine, ethanolamine, trimethamine, dicyclohexylamine, choline, and caffeine.

Additional pharmaceutically acceptable acids and bases useable with the present invention include those which are derived from the amino acids, for example, histidine, glycine, phenylalanine, aspartic acid, glutamic acid, lysine and asparagine.

"Pharmaceutically acceptable" buffers and salts include those derived from both acid and base addition salts of the above indicated acids and bases. Specific buffers and or salts include histidine, succinate and acetate.

A "lyoprotectant" is a molecule which, when combined with a protein of interest, significantly prevents or reduces chemical and/or physical instability of the protein upon lyophilization and subsequent storage. Exemplary lyoprotectants include sugars and their corresponding sugar alcohols; an amino acid such as monosodium glutamate or histidine; a methylamine such as betaine; a lyotropic salt such as magnesium sulfate; a polyol such as trihydric or higher molecular weight sugar alcohols, e.g. glycerin, dextran, erythritol, glycerol, arabitol, xylitol, sorbitol, and mannitol; propylene glycol; polyethylene glycol; Pluronics®; and combinations thereof. Additional exemplary lyoprotectants include glycerin and gelatin, and the sugars mellibiose, melezitose, raffinose, mannotriose and stachyose. Examples of reducing sugars include glucose, maltose, lactose, maltulose, iso-maltulose and lactulose. Examples of non-reducing sugars include non-reducing glycosides of polyhydroxy compounds selected from sugar alcohols and other straight chain polyalcohols. Preferred sugar alcohols are monoglycosides, especially those compounds obtained by reduction of disaccharides such as lactose, maltose, lactulose and maltulose. The glycosidic side group can be either glucosidic or galactosidic. Additional examples of sugar alcohols are glucitol, maltitol, lactitol and iso-maltulose. The preferred lyoprotectant are the non-reducing sugars trehalose or sucrose.

In preparing the reduced viscosity formulations of the invention, care should be taken using the above enumerated excipients as well as other additives, especially when added at high concentration, so as to not increase the viscosity of the formulation.

The lyoprotectant is added to the pre-lyophilized formulation in a "lyoprotecting amount" which means that, following lyophilization of the protein in the presence of the lyoprotecting amount of the lyoprotectant, the protein essentially retains its physical and chemical stability and integrity upon lyophilization and storage.

The "diluent" of interest herein is one which is pharmaceutically acceptable (safe and non-toxic for administration to a human) and is useful for the preparation of a liquid formulation, such as a formulation reconstituted after lyophilization. Exemplary diluents include sterile water, bacteriostatic water for injection (BWFI), a pH buffered solution (e.g. phosphate-buffered saline), sterile saline solution, Ringer's solution or dextrose solution. In an alternative embodiment, diluents can include aqueous solutions of salts and/or buffers.

A "preservative" is a compound which can be added to the formulations herein to reduce bacterial action. The addition of a preservative may, for example, facilitate the production of a multi-use (multiple-dose) formulation. Examples of potential preservatives include octadecyldimethylbenzyl ammonium chloride, hexamethonium chloride, benzalkonium chloride (a mixture of alkylbenzyldimethylammonium chlorides in which the alkyl groups are long-chain compounds), and benzethonium chloride. Other types of preservatives include aromatic alcohols such as phenol, butyl and benzyl alcohol, alkyl parabens such as methyl or propyl paraben, catechol, resorcinol, cyclohexanol, 3-pentanol, and m-cresol. The most preferred preservative herein is benzyl alcohol.

A "bulking agent" is a compound which adds mass to a lyophilized mixture and contributes to the physical structure of the lyophilized cake (e.g. facilitates the production of an essentially uniform lyophilized cake which maintains an open pore structure). Exemplary bulking agents include mannitol, glycine, polyethylene glycol and sorbitol. The liquid formulations of the present invention obtained by reconstitution of a lyophilized formulation may contain such bulking agents.

"Treatment" refers to both therapeutic treatment and prophylactic or preventative measures. Those in need of treatment include those already with the disorder as well as those in which the disorder is to be prevented.

"Mammal" for purposes of treatment refers to any animal classified as a mammal, including humans, domestic and farm animals, and zoo, sports, or pet animals, such as dogs, horses, rabbits, cattle, pigs, hamsters, mice, cats, etc. Preferably, the mammal is human.

A "disorder" is any condition that would benefit from treatment with the protein. This includes chronic and acute disorders or diseases including those pathological conditions which predispose the mammal to the disorder in question. Non-limiting examples of disorders to be treated herein include carcinomas and allergies.

A "therapeutically effective amount" is at least the minimum concentration required to effect a measurable improvement or prevention of a particular disorder. Therapeutically effective amounts of known proteins are well known in the art, while the effective amounts of proteins hereinafter discovered may be determined by standard techniques which are well within the skill of a skilled artisan, such as an ordinary physician.

"Viscosity" as used herein may be "kinematic viscosity" or "absolute viscosity." "Kinematic viscosity" is a measure of the resistive flow of a fluid under the influence of gravity. When two fluids of equal volume are placed in identical capillary viscometers and allowed to flow by gravity, a viscous fluid takes longer than a less viscous fluid to flow through the capillary. If one fluid takes 200 seconds to complete its flow and another fluid takes 400 seconds, the second fluid is twice as viscous as the first on a kinematic viscosity scale. "Absolute viscosity", sometimes called dynamic or simple viscosity, is the product of kinematic viscosity and fluid density:

$$\text{Absolute Viscosity} = \text{Kinematic Viscosity} \times \text{Density}$$

The dimension of kinematic viscosity is $L^2/T$ where L is a length and T is a time. Commonly, kinematic viscosity is expressed in centistokes (cSt). The SI unit of kinematic viscosity is $mm^2/s$, which is 1 cSt. Absolute viscosity is expressed in units of centipoise (cP). The SI unit of absolute viscosity is the milliPascal-second (mPa-s), where 1 cP=1 mPa-s.

II. Modes for Carrying Out the Invention

A. Protein Preparation

The protein to be formulated may be produced by any known technique, such as by culturing cells transformed or transfected with a vector containing nucleic acid encoding the protein, as is well known in art, or through synthetic techniques (such as recombinant techniques and peptide synthesis or a combination of these techniques) or may be isolated from an endogenous source of the protein.

Preparation of the protein to be formulated by the method of the invention by recombinant means may be accomplished by transfecting or transforming suitable host cells with expression or cloning vectors and cultured in conventional nutrient media modified as appropriate for inducing promoters, selecting transformants, or amplifying the genes encoding the desired sequences. The culture conditions, such as media, temperature, pH and the like, can be selected by the skilled artisan without undue experimentation. In general, principles, protocols, and practical techniques for maximizing the productivity of cell cultures can be found in *Mammalian Cell Biotechnology: A Practical Approach*, M. Butler, Ed. (IRL Press, 1991) and Sambrook et al., *Molecular Cloning: A Laboratory Manual*, New York: Cold Spring Harbor Press. Methods of transfection are known to the ordinarily skilled artisan, and include for example, $CaPO_4$ and $CaCl_2$ transfection, electroporation, microinjection, etc. Suitable techniques are also described in Sambrook et al., supra. Additional transfection techniques are described in Shaw et al., *Gene* 23: 315 (1983); WO 89/05859; Graham et al., *Virology* 52: 456-457 (1978) and U.S. Pat. No. 4,399,216.

The nucleic acid encoding the desired protein for formulation according to the present method may be inserted into a replicable vector for cloning or expression. Suitable vectors are publicly available and may take the form of a plasmid, cosmid, viral particle or phage. The appropriate nucleic acid sequence may be inserted into the vector by a variety of procedures. In general, DNA is inserted into an appropriate restriction endonuclease site(s) using techniques known in the art. Vector components generally include, but are not limited to, one or more of a signal sequence, an origin of replication, one or more marker genes, and enhancer element, a promoter, and a transcription termination sequence. Construction of suitable vectors containing one or more of these components employs standard ligation techniques which are known to the skilled artisan.

Forms of the protein to be formulated may be recovered from culture medium or from host cell lysates. If membrane-bound, it can be released from the membrane using a suitable detergent or through enzymatic cleavage. Cells employed for expression can also be disrupted by various physical or chemical means, such as freeze-thaw cycling, sonication, mechanical disruption or cell lysing agents.

Purification of the protein to be formulated may be effected by any suitable technique known in the art, such as for example, fractionation on an ion-exchange column, ethanol precipitation, reverse phase HPLC, chromatography on silica or cation-exchange resin (e.g., DEAE), chromatofocusing, SDS-PAGE, ammonium sulfate precipitation, gel filtration using protein A Sepharose columns (e.g., Sephadex® G-75) to remove contaminants such as IgG, and metal chelating columns to bind epitope-tagged forms.

B. Antibody Preparation

In certain embodiments of the invention, the protein of choice is an antibody. Techniques for the production of antibodies, including polyclonal, monoclonal, humanized, bispecific and heteroconjugate antibodies follow.

(i) Polyclonal Antibodies.

Polyclonal antibodies are generally raised in animals by multiple subcutaneous (sc) or intraperitoneal (ip) injections of the relevant antigen and an adjuvant. It may be useful to conjugate the relevant antigen to a protein that is immunogenic in the species to be immunized, e.g., keyhole limpet hemocyanin, serum albumin, bovine thyroglobulin, or soybean trypsin inhibitor. Examples of adjuvants which may be employed include Freund's complete adjuvant and MPL-TDM adjuvant (monophosphoryl Lipid A, synthetic trehalose dicorynomycolate). The immunization protocol may be selected by one skilled in the art without undue experimentation.

One month later the animals are boosted with $\frac{1}{5}$ to $\frac{1}{10}$ the original amount of peptide or conjugate in Freund's complete adjuvant by subcutaneous injection at multiple sites. Seven to 14 days later the animals are bled and the serum is assayed for antibody titer. Animals are boosted until the titer plateaus. Preferably, the animal is boosted with the conjugate of the same antigen, but conjugated to a different protein and/or through a different cross-linking reagent. Conjugates also can be made in recombinant cell culture as protein fusions. Also, aggregating agents such as alum are suitably used to enhance the immune response.

(ii) Monoclonal Antibodies.

Monoclonal antibodies are obtained from a population of substantially homogeneous antibodies, i.e., the individual antibodies comprising the population are identical except for possible naturally occurring mutations that may be present in minor amounts. Thus, the modifier "monoclonal" indicates the character of the antibody as not being a mixture of discrete antibodies.

For example, the monoclonal antibodies may be made using the hybridoma method first described by Kohler et al., *Nature*, 256:495 (1975), or may be made by recombinant DNA methods (U.S. Pat. No. 4,816,567).

In the hybridoma method, a mouse or other appropriate host animal, such as a hamster, is immunized as hereinabove described to elicit lymphocytes that produce or are capable of producing antibodies that will specifically bind to the protein used for immunization. Alternatively, lymphocytes may be immunized in vitro. Lymphocytes then are fused with myeloma cells using a suitable fusing agent, such as polyethylene glycol, to form a hybridoma cell (Goding, *Monoclonal Antibodies: Principles and Practice*, pp. 59-103 (Academic Press, 1986).

The immunizing agent will typically include the protein to be formulated. Generally either peripheral blood lymphocytes ("PBLs") are used if cells of human origin are desired, or spleen cells or lymph node cells are used if non-human mammalian sources are desired. The lymphoctyes are then fused with an immortalized cell line using a suitable fusing agent, such as polyethylene glycol, to form a hybridoma cell. Goding, *Monoclonal antibodies: Principles and Practice*, Academic Press (1986), pp. 59-103. Immortalized cell lines are usually transformed mammalian cell, particularly myeloma cells of rodent, bovine and human origin. Usually, rat or mouse myeloma cell lines are employed. The hybridoma cells thus prepared are seeded and grown in a suitable culture medium that preferably contains one or more substances that inhibit the growth or survival of the unfused, parental myeloma cells. For example, if the parental myeloma cells lack the enzyme hypoxanthine guanine phosphoribosyl transferase (HGPRT or HPRT), the culture medium for the hybridomas typically will include hypoxanthine, aminopterin, and thymidine (HAT medium), which substances prevent the growth of HGPRT-deficient cells.

Preferred myeloma cells are those that fuse efficiently, support stable high-level production of antibody by the selected antibody-producing cells, and are sensitive to a medium such as HAT medium. Among these, preferred myeloma cell lines are murine myeloma lines, such as those derived from MOPC-21 and MPC-11 mouse tumors available from the Salk Institute Cell Distribution Center, San Diego, Calif. USA, and SP-2 cells available from the American Type Culture Collection, Rockville, Md. USA. Human myeloma and mouse-human heteromyeloma cell lines also have been described for the production of human monoclonal antibodies (Kozbor, *J. Immunol.*, 133:3001 (1984); Brodeur et al., *Monoclonal Antibody Production Techniques and Applications*, pp. 51-63 (Marcel Dekker, Inc., New York, 1987)).

Culture medium in which hybridoma cells are growing is assayed for production of monoclonal antibodies directed against the antigen. Preferably, the binding specificity of monoclonal antibodies produced by hybridoma cells is determined by immunoprecipitation or by an in vitro binding assay, such as radioimmunoassay (RIA) or enzyme-linked immunoabsorbent assay (ELISA).

The binding affinity of the monoclonal antibody can, for example, be determined by the Scatchard analysis of Munson et al., *Anal. Biochem.*, 107:220 (1980).

After hybridoma cells are identified that produce antibodies of the desired specificity, affinity, and/or activity, the clones may be subcloned by limiting dilution procedures and grown by standard methods (Goding, supra). Suitable culture media for this purpose include, for example, D-MEM or RPMI-1640 medium. In addition, the hybridoma cells may be grown in vivo as ascites tumors in an animal.

The immunizing agent will typically include the epitope protein to which the antibody binds. Generally, either peripheral blood lymphocytes ("PBLs") are used if cells of human origin are desired, or spleen cells or lymph node cells are used if non-human mammalian sources are desired. The lymphocytes are then fused with an immortalized cell line using a suitable fusing agent, such as polyethylene glycol, to form a hybridoma cell. Goding, *Monoclonal Antibodies: Principals and Practice*, Academic Press (1986), pp. 59-103.

Immortalized cell lines are usually transformed mammalian cells, particularly mycloma cells of rodent, bovine and human origin. Usually, rat or mouse myclome cell lines are employed. The hybridoma cells may be cultured in a suitable culture medium that preferably contains one or more substances that inhibit the growth or survival of the unfused, immortalized cells. For example, if the parental cells lack the enzyme hypoxanthine guanine phosphoribosyl transferase (HGPRT or HPRT), the culture medium for the hybridomas typically will include hypoxanthine, aminopterin and thymidine ("HAT medium"), which substances prevent the growth of HGPRT-deficient cells.

Preferred immortalized cell lines are those that fuse efficiently, support stable high level expression of antibody by the selected antibody-producing cells, and are sensitive to a medium such as HAT medium. More preferred immortalized cell lines are murine mycloma lines, which can be obtained, for instance, from the Salk Institute Cell Distribution Center, San Diego, Calif. and the American Type Culture Collection, Rockville, Md. Human myeloma and mouse-human heteromyeloma cell lines also have been described for the production of human monoclonal antibodies. Kozbor, *J. Immunol.*, 133:3001 (1984); Brodeur et al., *Monoclonal Antibody Production Techniques and Applications*, Marcel Dekker, Inc., New York, (1987) pp. 51-63.

The culture medium in which the hybridoma cells are cultured can then be assayed for the presence of monoclonal antibodies directed against the protein to be formulated. Preferably, the binding specificity of monoclonal antibodies produced by the hybridoma cells is determined by immunoprecipitation or by an in vitro binding assay, such as radioimmunoassay (RIA) or enzyme-linked immunoabsorbent assay (ELISA). Such techniques and assays are known in the art. The binding affinity of the monoclonal antibody can, for example, be determined by the Scatchard analysis of Munson and Pollard, *Anal. Biochem.*, 107:220 (1980).

After the desired hybridoma cells are identified, the clones may be subcloned by limiting dilution procedures and grown by standard methods. Goding, supra. Suitable culture media for this purpose include, for example, Dulbecco's Modified Eagle's Medium and RPMI-1640 medium. Alternatively, the hybridoma cells may be grown in vivo as ascites in a mammal.

The monoclonal antibodies secreted by the subclones are suitably separated from the culture medium, ascites fluid, or serum by conventional immunoglobulin purification procedures such as, for example, protein A-Sepharose, hydroxylapatite chromatography, gel electrophoresis, dialysis, or affinity chromatography.

DNA encoding the monoclonal antibodies is readily isolated and sequenced using conventional procedures (e.g., by using oligonucleotide probes that are capable of binding specifically to genes encoding the heavy and light chains of murine antibodies). The hybridoma cells serve as a preferred source of such DNA. Once isolated, the DNA may be placed into expression vectors, which are then transfected into host cells such as *E. coli* cells, simian COS cells, Chinese hamster ovary (CHO) cells, or myeloma cells that do not otherwise produce immunoglobulin protein, to obtain the synthesis of monoclonal antibodies in the recombinant host cells. Review articles on recombinant expression in bacteria of DNA encoding the antibody include Skerra et al., *Curr. Opinion in Immunol.*, 5:256-262 (1993) and Plückthun, *Immunol. Revs.* 130:151-188 (1992).

In a further embodiment, antibodies can be isolated from antibody phage libraries generated using the techniques described in McCafferty et al., *Nature*, 348:552-554 (1990). Clackson et al., *Nature*, 352:624-628 (1991) and Marks et al., *J. Mol. Biol.*, 222:581-597 (1991) describe the isolation of murine and human antibodies, respectively, using phage libraries. Subsequent publications describe the production of high affinity (nM range) human antibodies by chain shuffling (Marks et al., *Bio/Technology*, 10:779-783 (1992)), as well as combinatorial infection and in vivo recombination as a strategy for constructing very large phage libraries (Waterhouse et al., *Nuc. Acids. Res.*, 21:2265-2266 (1993)). Thus, these techniques are viable alternatives to traditional monoclonal antibody hybridoma techniques for isolation of monoclonal antibodies.

The DNA also may be modified, for example, by substituting the coding sequence for human heavy- and light-chain constant domains in place of the homologous murine sequences (U.S. Pat. No. 4,816,567; Morrison, et al., *Proc. Natl. Acad. Sci. USA*, 81:6851 (1984)), or by covalently joining to the immunoglobulin coding sequence all or part of the coding sequence for a non-immunoglobulin polypeptide.

Typically such non-immunoglobulin polypeptides are substituted for the constant domains of an antibody, or they are substituted for the variable domains of one antigen-combining site of an antibody to create a chimeric bivalent antibody comprising one antigen-combining site having specificity for an antigen and another antigen-combining site having specificity for a different antigen.

Chimeric or hybrid antibodies also may be prepared in vitro using known methods in synthetic protein chemistry, including those involving crosslinking agents. For example, immunotoxins may be constructed using a disulfide-exchange reaction or by forming a thioether bond. Examples of suitable reagents for this purpose include iminothiolate and methyl-4-mercaptobutyrimidate.

(iii) Humanized and Human Antibodies.

The antibodies subject to the formulation method may further comprise humanized or human antibodies. Humanized forms of non-human (e.g., murine) antibodies are chimeric immunoglobulins, immunoglobulin chains or fragments thereof (such as Fv, Fab, Fab', F(ab')$_2$ or other antigen-binding subsequences of antibodies) which contain minimal sequence derived from non-human immunoglobulin. Humanized antibodies include human immunoglobulins (recipient antibody) in which residues from a complementarity determining region (CDR) of the recipient are replaced by residues from a CDR of a non-human species (donor antibody) such as mouse, rat or rabbit having the desired specificity, affinity and capacity. In some instances, Fv framework residues of the human immunoglobulin are replaced by corresponding non-human residues. Humanized antibodies may also comprise residues which are found neither in the recipient antibody nor in the imported CDR or framework sequences. In general, the humanized antibody will comprise substantially all of at least one, and typically two, variable domain, in which all or substantially all of the CDR regions correspond to those of a non-human immunoglobulin and all or substantially all of the FR regions are those of a human immunoglobulin consensus sequence. The humanized antibody optimally also will comprise at least a portion of an immunoglobulin constant region (Fc), typically that of a human immunoglobulin. Jones et al., *Nature* 321: 522-525 (1986); Riechmann et al., *Nature* 332: 323-329 (1988) and Presta, *Curr. Opin. Struct. Biol.* 2: 593-596 (1992).

Methods for humanizing non-human antibodies are well known in the art. Generally, a humanized antibody has one or more amino acid residues introduced into it from a source which is non-human. These non-human amino acid residues are often referred to as "import" residues, which are typically taken from an "import" variable domain. Humanization can be essentially performed following the method of Winter and co-workers, Jones et al., *Nature* 321:522-525 (1986); Riechmann et al., *Nature* 332:323-327 (1988); Verhoeyen et al., *Science* 239:1534-1536 (1988), or through substituting rodent CDRs or CDR sequences for the corresponding sequences of a human antibody. Accordingly, such "humanized" antibodies are chimeric antibodies (U.S. Pat. No. 4,816,567), wherein substantially less than an intact human variable domain has been substituted by the corresponding sequence from a non-human species. In practice, humanized antibodies are typically human antibodies in which some CDR residues and possibly some FR residues are substituted by residues from analogous sites in rodent antibodies.

The choice of human variable domains, both light and heavy, to be used in making the humanized antibodies is very important to reduce antigenicity. According to the so-called "best-fit" method, the sequence of the variable domain of a rodent antibody is screened against the entire library of known human variable-domain sequences. The human sequence which is closest to that of the rodent is then accepted as the human framework (FR) for the humanized antibody. Sims et al., *J. Immunol.*, 151:2296 (1993); Chothia et al., *J. Mol. Biol.*, 196:901 (1987). Another method uses a particular framework derived from the consensus sequence of all human antibodies of a particular subgroup of light or heavy chains. The same framework may be used for several different humanized antibodies. Carter et al., *Proc. Natl. Acad. Sci. USA*, 89:4285 (1992); Presta et al., *J. Immunol.*, 151:2623 (1993).

It is further important that antibodies be humanized with retention of high affinity for the antigen and other favorable biological properties. To achieve this goal, according to a preferred method, humanized antibodies are prepared by a process of analysis of the parental sequences and various conceptual humanized products using three-dimensional models of the parental and humanized sequences. Three-dimensional immunoglobulin models are commonly available and are familiar to those skilled in the art. Computer programs are available which illustrate and display probable three-dimensional conformational structures of selected candidate immunoglobulin sequences. Inspection of these displays permits analysis of the likely role of the residues in the functioning of the candidate immunoglobulin sequence, i.e., the analysis of residues that influence the ability of the candidate immunoglobulin to bind its antigen. In this way, FR residues can be selected and combined from the recipient and import sequences so that the desired antibody characteristic, such as increased affinity for the target antigen(s), is achieved. In general, the CDR residues are directly and most substantially involved in influencing antigen binding.

Alternatively, it is now possible to produce transgenic animals (e.g., mice) that are capable, upon immunization, of producing a full repertoire of human antibodies in the absence of endogenous immunoglobulin production. For example, it has been described that the homozygous deletion of the antibody heavy-chain joining region ($J_H$) gene in chimeric and germ-line mutant mice results in complete inhibition of endogenous antibody production. Transfer of the human germ-line immunoglobulin gene array in such germ-line mutant mice will result in the production of human antibodies upon antigen challenge. See, e.g., Jakobovits et al., *Proc. Natl. Acad. Sci. USA*, 90:2551 (1993); Jakobovits et al., *Nature*, 362:255-258 (1993); Bruggermann et al., *Year in Immuno.*, 7:33 (1993). Human antibodies can also be derived from phage-display libraries (Hoogenboom et al., *J. Mol. Biol.*, 227:381 (1991); Marks et al., *J. Mol. Biol.*, 222:581-597 (1991)).

Human antibodies can also be produced using various techniques known in the art, including phage display libraries. Hoogenboom and Winter, *J. Mol. Biol.* 227: 381 (1991); Marks et al., *J. Mol. Biol.* 222: 581 (1991). The techniques of Cole et al., and Boerner et al., are also available for the preparation of human monoclonal antibodies (Cole et al., Monoclonal Antibodies and Cancer Therapy, Alan R. Liss, p. 77 (1985) and Boerner et al., *J. Immunol.* 147(1): 86-95 (1991). Similarly, human antibodies can be made by introducing human immunoglobulin loci into transgenic animals, e.g., mice in which the endogenous immunoglobulin genes have been partially or completely inactivated. Upon challenge, human antibody production is observed, which closely resemble that seen in human in all respects, including gene rearrangement, assembly and antibody repertoire. This approach is described, for example, in U.S. Pat. Nos. 5,545,807; 5,545,806, 5,569,825, 5,625,126, 5,633,425, 5,661,016 and in the following scientific publications: Marks et al., *Bio/Technology* 10: 779-783 (1992); Lonberg et al., *Nature* 368: 856-859 (1994); Morrison, *Nature* 368:

812-13 (1994), Fishwild et al., *Nature Biotechnology* 14: 845-51 (1996), Neuberger, *Nature Biotechnology* 14: 826 (1996) and Lonberg and Huszar, *Intern. Rev. Immunol.* 13: 65-93 (1995).

(iv) Antibody Dependent Enzyme-Mediated Prodrug Therapy (ADEPT)

The antibodies of the present invention may also be used in ADEPT by conjugating the antibody to a prodrug-activating enzyme which converts a prodrug (e.g. a peptidyl chemotherapeutic agent, see WO 81/01145) to an active anti-cancer drug. See, for example, WO 88/07378 and U.S. Pat. No. 4,975,278.

The enzyme component of the immunoconjugate useful for ADEPT includes any enzyme capable of acting on a prodrug in such as way so as to convert it into its more active, cytotoxic form.

Enzymes that are useful in the method of this invention include, but are not limited to, glycosidase, glucose oxidase, human lysozyme, human glucuronidase, alkaline phosphatase useful for converting phosphate-containing prodrugs into free drugs; arylsulfatase useful for converting sulfate-containing prodrugs into free drugs; cytosine deaminase useful for converting non-toxic 5-fluorocytosine into the anti-cancer drug 5-fluorouracil; proteases, such as serratia protease, thermolysin, subtilisin, carboxypeptidases (e.g., carboxypeptidase G2 and carboxypeptidase A) and cathepsins (such as cathepsins B and L), that are useful for converting peptide-containing prodrugs into free drugs; D-alanylcarboxypeptidases, useful for converting prodrugs that contain D-amino acid substituents; carbohydrate-cleaving enzymes such as β-galactosidase and neuraminidase useful for converting glycosylated prodrugs into free drugs; β-lactamase useful for converting drugs derivatized with β-lactams into free drugs; and penicillin amidases, such as penicillin V amidase or penicillin G amidase, useful for converting drugs derivatized at their amine nitrogens with phenoxyacetyl or phenylacetyl groups, respectively, into free drugs. Alternatively, antibodies with enzymatic activity, also known in the art as "abzymes" can be used to convert the prodrugs of the invention into free active drugs (see, e.g., Massey, *Nature* 328: 457-458 (1987)). Antibody-abzyme conjugates can be prepared as described herein for delivery of the abzyme to a tumor cell population.

The enzymes of this invention can be covalently bound to the anti-IL-17 or anti-LIF antibodies by techniques well known in the art such as the use of the heterobifunctional cross-linking agents discussed above. Alternatively, fusion proteins comprising at least the antigen binding region of the antibody of the invention linked to at least a functionally active portion of an enzyme of the invention can be constructed using recombinant DNA techniques well known in the art (see, e.g. Neuberger et al., *Nature* 312: 604-608 (1984)).

(iv) Bispecific and Polyspecific Antibodies

Bispecific antibodies (BsAbs) are antibodies that have binding specificities for at least two different epitopes. Such antibodies can be derived from full length antibodies or antibody fragments (e.g. F(ab')$_2$ bispecific antibodies).

Methods for making bispecific antibodies are known in the art. Traditional production of full length bispecific antibodies is based on the coexpression of two immunoglobulin heavy chain-light chain pairs, where the two chains have different specificities. Millstein et al., *Nature*, 305:537-539 (1983). Because of the random assortment of immunoglobulin heavy and light chains, these hybridomas (quadromas) produce a potential mixture of 10 different antibody molecules, of which only one has the correct bispecific structure. Purification of the correct molecule, which is usually done by affinity chromatography steps, is rather cumbersome, and the product yields are low. Similar procedures are disclosed in WO 93/08829 and in Traunecker et al., *EMBO J.*, 10:3655-3659 (1991).

Antibody variable domains with the desired binding specificities (antibody-antigen combining sites) can be fused to immunoglobulin constant domain sequences. The fusion preferably is with an immunoglobulin heavy-chain constant domain, comprising at least part of the hinge, CH2, and CH3 regions. It is preferred to have the first heavy-chain constant region (CH1) containing the site necessary for light-chain binding present in at least one of the fusions. DNAs encoding the immunoglobulin heavy-chain fusions, and, if desired, the immunoglobulin light chain, are inserted into separate expression vectors, and are co-transfected into a suitable host organism. For further details of generating bispecific antibodies, see, for example, Suresh et al., *Methods in Enzymology* 121: 210 (1986).

According to a different approach, antibody variable domains with the desired binding specificities (antibody-antigen combining sites) are fused to immunoglobulin constant domain sequences. The fusion preferably is with an immunoglobulin heavy chain constant domain, comprising at least part of the hinge, CH2, and CH3 regions. It is preferred to have the first heavy-chain constant region (CH1) containing the site necessary for light chain binding, present in at least one of the fusions. DNAs encoding the immunoglobulin heavy chain fusions and, if desired, the immunoglobulin light chain, are inserted into separate expression vectors, and are co-transfected into a suitable host organism. This provides for great flexibility in adjusting the mutual proportions of the three polypeptide fragments in embodiments when unequal ratios of the three polypeptide chains used in the construction provide the optimum yields. It is, however, possible to insert the coding sequences for two or all three polypeptide chains in one expression vector when the expression of at least two polypeptide chains in equal ratios results in high yields or when the ratios are of no particular significance.

According to another approach described in WO 96/27011, the interface between a pair of antibody molecules can be engineered to maximize the percentage of heterodimers which are recovered from recombinant cell culture. The preferred interface comprises at least a part of the CH3 region of an antibody constant domain. In this method, one or more small amino acid side chains from the interface of the first antibody molecule are replaced with larger side chains (e.g., tyrosine or tryptophan). Compensatory "cavities" of identical or similar size to the large side chains(s) are created on the interface of the second antibody molecule by replacing large amino acid side chains with smaller ones (e.g., alanine or threonine). This provides a mechanism for increasing the yield of the heterodimer over other unwanted end-products such as homodimers.

In a preferred embodiment of this approach, the bispecific antibodies are composed of a hybrid immunoglobulin heavy chain with a first binding specificity in one arm, and a hybrid immunoglobulin heavy chain-light chain pair (providing a second binding specificity) in the other arm. It was found that this asymmetric structure facilitates the separation of the desired bispecific compound from unwanted immunoglobulin chain combinations, as the presence of an immunoglobulin light chain in only one half of the bispecific molecule provides for a facile way of separation. This approach is disclosed in WO 94/04690, published Mar. 3, 1994. For further details of generating bispecific antibodies see, for example, Suresh et al., *Methods in Enzymology*, 121:210 (1986).

Bispecific antibodies include cross-linked or "heteroconjugate" antibodies. For example, one of the antibodies in the heteroconjugate can be coupled to avidin, the other to biotin. Such antibodies have, for example, been proposed to target immune system cells to unwanted cells (U.S. Pat. No. 4,676,980), and for treatment of HIV infection (WO 91/00360, WO 92/200373). Heteroconjugate antibodies may be made using any convenient cross-linking methods. Suitable cross-linking agents are well known in the art, and are disclosed in U.S. Pat. No. 4,676,980, along with a number of cross-linking techniques.

Techniques for generating bispecific antibodies from antibody fragments have also been described in the literature. The following techniques can also be used for the production of bivalent antibody fragments which are not necessarily bispecific. For example, Fab' fragments recovered from *E. coli* can be chemically coupled in vitro to form bivalent antibodies. See, Shalaby et al., *J. Exp. Med.,* 175:217-225 (1992).

Bispecific antibodies can be prepared as full length antibodies or antibody fragments (e.g. F(ab')$_2$ bispecific antibodies). Techniques for generating bispecific antibodies from antibody fragments have been described in the literature. For example, bispecific antibodies can be prepared using chemical linkage. Brennan et al., *Science* 229: 81 (1985) describe a procedure wherein intact antibodies are proteolytically cleaved to generate F(ab')$_2$ fragments. These fragments are reduced in the presence of the dithiol complexing agent sodium arsenite to stabilize vicinal dithiols and prevent intermolecular disulfide formation. The Fab' fragments generated are then converted to thionitrobenzoate (TNB) derivatives. One of the Fab'-TNB derivatives is then reconverted to the Fab'-TNB derivative to form the bispecific antibody. The bispecific antibodies produced can be used as agents for the selective immobilization of enzymes.

Fab' fragments may be directly recovered from *E. coli* and chemically coupled to form bispecific antibodies. Shalaby et al., *J. Exp. Med.* 175: 217-225 (1992) describes the production of fully humanized bispecific antibody F(ab')$_2$ molecules. Each Fab' fragment was separately secreted from *E. coli* and subjected to directed chemical coupling in vitro to form the bispecific antibody. The bispecific antibody thus formed was able to bind to cells overexpressing the ErbB2 receptor and normal human T cells, as well as trigger the lytic activity of human cytotoxic lymphocytes against human breast tumor targets.

Various techniques for making and isolating bivalent antibody fragments directly from recombinant cell culture have also been described. For example, bivalent heterodimers have been produced using leucine zippers. Kostelny et al., *J. Immunol.,* 148(5):1547-1553 (1992). The leucine zipper peptides from the Fos and Jun proteins were linked to the Fab' portions of two different antibodies by gene fusion. The antibody homodimers were reduced at the hinge region to form monomers and then re-oxidized to form the antibody heterodimers. The "diabody" technology described by Hollinger et al., *Proc. Natl. Acad. Sci. USA,* 90: 6444-6448 (1993) has provided an alternative mechanism for making bispecific/bivalent antibody fragments. The fragments comprise a heavy-chain variable domain (V$_H$) connected to a light-chain variable domain (V$_L$) by a linker which is too short to allow pairing between the two domains on the same chain. Accordingly, the V$_H$ and V$_L$ domains of one fragment are forced to pair with the complementary V$_L$ and V$_H$ domains of another fragment, thereby forming two antigen-binding sites. Another strategy for making bispecific/bivalent antibody fragments by the use of single-chain Fv (sFv) dimers has also been reported. See Gruber et al., *J. Immunol.,* 152:5368 (1994).

Antibodies with more than two valencies are contemplated. For example, trispecific antibodies can be prepared. Tutt et al., *J. Immunol.* 147: 60 (1991).

Exemplary bispecific antibodies may bind to two different epitopes on a given molecule. Alternatively, an anti-protein arm may be combined with an arm which binds to a triggering molecule on a leukocyte such as a T-cell receptor molecule (e.g., CD2, CD3, CD28 or B7), or Fc receptors for IgG (FcγR), such as FcγRI (CD64), FcγRII (CD32) and FcγRIII (CD16) so as to focus cellular defense mechanisms to the cell expressing the particular protein. Bispecific antibocis may also be used to localize cytotoxic agents to cells which express a particular protein. Such antibodies possess a protein-binding arm and an arm which binds a cytotoxic agent or a radionuclide chelator, such as EOTUBE, DPTA, DOTA or TETA. Another bispecific antibody of interest binds the protein of interest and further binds tissue factor (TF).

(v) Heteroconjugate Antibodies

Heteroconjugate antibodies are also within the scope of the present invention. Heteroconjugate antibodies are composed of two covalently joined antibodies. Such antibodies have, for example, been proposed to target immune system cells to unwanted cells, U.S. Pat. No. 4,676,980, and for treatment of HIV infection. WO 91/00360, WO 92/200373 and EP 03089. It is contemplated that the antibodies may be prepared in vitro using known methods in synthetic protein chemistry, including those involving crosslinking agents. For example, immunotoxins may be constructed using a disulfide exchange reaction or by forming a thioether bond. Examples of suitable reagents for this purpose include iminothiolate and methyl-4-mercaptobutyrimidate and those disclosed, for example, in U.S. Pat. No. 4,676,980.

B. Preparation of Lyophilized Formulations

Although the formulations herein are not limited to reconstituted lyophilized formulations, in a particular embodiment, the proteins are lyophilized and then reconstituted to produce the reduced-viscosity stable liquid formulations of the invention. In this particular embodiment, after preparation of the protein of interest as described above, a "pre-lyophilized formulation" is produced. The amount of protein present in the pre-lyophilized formulation is determined taking into account the desired dose volumes, mode(s) of administration etc. For example, the starting concentration of an intact antibody can be from about 2 mg/ml to about 50 mg/ml, preferably from about 5 mg/ml to about 40 mg/ml and most preferably from about 20-30 mg/ml.

The protein to be formulated is generally present in solution. For example, in the elevated ionic strength reduced viscosity formulations of the invention, the protein may be present in a pH-buffered solution at a pH from about 4-8, and preferably from about 5-7. The buffer concentration can be from about 1 mM to about 20 mM, alternatively from about 3 mM to about 15 mM, depending, for example, on the buffer and the desired tonicity of the formulation (e.g. of the reconstituted formulation). Exemplary buffers and/or salts are those which are pharmaceutically acceptable and may be created from suitable acids, bases and salts thereof, such as those which are defined under "pharmaceutically acceptable" acids, bases or buffers.

In one embodiment, a lyoprotectant is added to the pre-lyophilized formulation. The amount of lyoprotectant in the pre-lyophilized formulation is generally such that, upon reconstitution, the resulting formulation will be isotonic. However, hypertonic reconstituted formulations may also be suitable. In addition, the amount of lyoprotectant must not be too low such that an unacceptable amount of degradation/ aggregation of the protein occurs upon lyophilization. However, exemplary lyoprotectant concentrations in the pre-lyophilized formulation are from about 10 mM to about 400 mM, alternatively from about 30 mM to about 300 mM, alternatively from about 50 mM to about 100 mM. Examplery lyoprotectants include sugars and sugar alcohols such as sucrose, mannose, trehalose, glucose, sorbitol, mannitol. However, under particular circumstances, certain lyoprotectants may also contribute to an increase in viscosity of the formulation. As such, care should be taken so as to select particular lyoprotectants which minimize or neutralize this effect. Additional lyoprotectants are described above under the definition of "lyoprotectants".

The ratio of protein to lyoprotectant can vary for each particular protein or antibody and lyoprotectant combination. In the case of an antibody as the protein of choice and a sugar (e.g., sucrose or trehalose) as the lyoprotectant for generating an isotonic reconstituted formulation with a high protein concentration, the molar ratio of lyoprotectant to antibody may be from about 100 to about 1500 moles lyoprotectant to 1 mole antibody, and preferably from about 200 to about 1000 moles of lyoprotectant to 1 mole antibody, for example from about 200 to about 600 moles of lyoprotectant to 1 mole antibody.

In a preferred embodiment, it may be desirable to add a surfactant to the pre-lyophilized formulation. Alternatively, or in addition, the surfactant may be added to the lyophilized formulation and/or the reconstituted formulation. Exemplary surfactants include nonionic surfactants such as polysorbates (e.g. polysorbates 20 or 80); polyoxamers (e.g. poloxamer 188); Triton; sodium octyl glycoside; lauryl-, myristyl-, linoleyl-, or stearyl-sulfobetaine; lauryl-, myristyl-, linoleyl- or stearyl-sarcosine; linoleyl-, myristyl-, or cetyl-betaine; lauroamidopropyl-, cocamidopropyl-, linoleamidopropyl-, myristamidopropyl-, palmidopropyl-, or isostearamidopropyl-betaine (e.g. lauroamidopropyl); myristamidopropyl-, palmidopropyl-, or isostearamidopropyl-dimethylamine; sodium methyl cocoyl-, or disodium methyl oleyl-taurate; and the MONAQUA™ series (Mona Industries, Inc., Paterson, N.J.), polyethyl glycol, polypropyl glycol, and copolymers of ethylene and propylene glycol (e.g. Pluronics, PF68 etc). The amount of surfactant added is such that it reduces particulate formation of the reconstituted protein and minimizes the formation of particulates after reconstitution. For example, the surfactant may be present in the pre-lyophilized formulation in an amount from about 0.001-0.5%, alternatively from about 0.005-0.05%.

A mixture of the lyoprotectant (such as sucrose or trehalose) and a bulking agent (e.g. mannitol or glycine) may be used in the preparation of the pre-lyophilization formulation. The bulking agent may allow for the production of a uniform lyophilized cake without excessive pockets therein etc. Other pharmaceutically acceptable carriers, excipients or stabilizers such as those described in Remington's Pharmaceutical Sciences 16th edition, Osol, A. Ed. (1980) may be included in the pre-lyophilized formulation (and/or the lyophilized formulation and/or the reconstituted formulation) provided that they do not adversely affect the desired characteristics of the formulation. Acceptable carriers, excipients or stabilizers are nontoxic to recipients at the dosages and concentrations employed and include; additional buffering agents; preservatives; co-solvents; antioxidants including ascorbic acid and methionine; chelating agents such as EDTA; metal complexes (e.g. Zn-protein complexes); biodegradable polymers such as polyesters; and/or salt-forming counterions such as sodium.

The formulation herein may also contain more than one protein as necessary for the particular indication being treated, preferably those with complementary activities that do not adversely affect the other protein. For example, it may be desirable to provide two or more antibodies which bind to the HER2 receptor or IgE in a single formulation. Such proteins are suitably present in combination in amounts that are effective for the purpose intended.

The formulations to be used for in vivo administration must be sterile. This is readily accomplished by filtration through sterile filtration membranes, prior to, or following, lyophilization and reconstitution. Alternatively, sterility of the entire mixture may be accomplished by autoclaving the ingredients, except for protein, at about 120° C. for about 30 minutes, for example.

After the protein, optional lyoprotectant and other optional components are mixed together, the formulation is lyophilized. Many different freeze-dryers are available for this purpose such as Hull50™ (Hull, USA) or GT20™ (Leybold-Heraeus, Germany) freeze-dryers. Freeze-drying is accomplished by freezing the formulation and subsequently subliming ice from the frozen content at a temperature suitable for primary drying. Under this condition, the product temperature is below the eutectic point or the collapse temperature of the formulation. Typically, the shelf temperature for the primary drying will range from about −30 to 25° C. (provided the product remains frozen during primary drying) at a suitable pressure, ranging typically from about 50 to 250 mTorr. The formulation, size and type of the container holding the sample (e.g., glass vial) and the volume of liquid will mainly dictate the time required for drying, which can range from a few hours to several days (e.g. 40-60 hrs). Optionally, a secondary drying stage may also be performed depending upon the desired residual moisture level in the product. The temperature at which the secondary drying is carried out ranges from about 0-40° C., depending primarily on the type and size of container and the type of protein employed. For example, the shelf temperature throughout the entire water removal phase of lyophilization may be from about 15-30° C. (e.g., about 20° C.). The time and pressure required for secondary drying will be that which produces a suitable lyophilized cake, dependent, e.g., on the temperature and other parameters. The secondary drying time is dictated by the desired residual moisture level in the product and typically takes at least about 5 hours (e.g. 10-15 hours). The pressure may be the same as that employed during the primary drying step. Freeze-drying conditions can be varied depending on the formulation and vial size.

C. Reconstitution of a Lyophilized Formulation

Prior to administration to the patient, the lyophilized formulation is reconstituted with a pharmaceutically acceptable diluent such that the protein concentration in the reconstituted formulation is at least about 50 mg/ml, for example from about 50 mg/ml to about 400 mg/ml, alternatively from about 80 mg/ml to about 300 mg/ml, alternatively from about 90 mg/ml to about 150 mg/ml. Such high protein concentrations in the reconstituted formulation are considered to be particularly useful where subcutaneous delivery of the reconstituted formulation is intended. However, for other routes of administration, such as intravenous administration, lower concentrations of the protein in the reconstituted formulation may be desired (for example from about 5-50 mg/ml, or from about 10-40 mg/ml protein in the reconstituted formulation). In certain embodiments, the protein concentration in the reconstituted formulation is significantly higher than that in the pre-lyophilized formulation. For example, the protein concentration in the reconstituted formulation may be about 2-40 times, alternatively 3-10 times, alternatively 3-6 times (e.g. at least three fold or at least four fold) that of the pre-lyophilized formulation.

Reconstitution generally takes place at a temperature of about 25° C. to ensure complete hydration, although other temperatures may be employed as desired. The time required for reconstitution will depend, e.g., on the type of diluent, amount of excipient(s) and protein. Exemplary diluents include sterile water, bacteriostatic water for injection (BWFI), a pH buffered solution (e.g. phosphate-buffered saline), sterile saline solution, Ringer's solution or dextrose solution. The diluent optionally contains a preservative. Exemplary preservatives have been described above, with aromatic alcohols such as benzyl or phenol alcohol being the preferred preservatives. The amount of preservative employed is determined by assessing different preservative concentrations for compatibility with the protein and preservative efficacy testing. For example, if the preservative is an aromatic alcohol (such as benzyl alcohol), it can be present in an amount from about 0.1-2.0% and preferably from about 0.5-1.5%, but most preferably about 1.0-1.2%.

Preferably, the reconstituted formulation has less than 6000 particles per vial which are ≥10 μm in size.

D. Administration of the Formulation

The formulations of the present invention, including but not limited to reconstituted formulations, are administered to a mammal in need of treatment with the protein, preferably a human, in accord with known methods, such as intravenous administration as a bolus or by continuous infusion over a period of time, by intramuscular, intraperitoneal, intracerobrospinal, subcutaneous, intra-articular, intrasynovial, intrathecal, oral, topical, or inhalation routes.

In preferred embodiments, the formulations are administered to the mammal by subcutaneous (i.e. beneath the skin) administration. For such purposes, the formulation may be injected using a syringe. However, other devices for administration of the formulation are available such as injection devices (e.g. the Inject-Ease™ and Genject devices); injector pens (such as the GenPen); needleless devices (e.g. MediJector and BioJector); and subcutaneous patch delivery systems.

The appropriate dosage ("therapeutically effective amount") of the protein will depend, for example, on the condition to be treated, the severity and course of the condition, whether the protein is administered for preventive or therapeutic purposes, previous therapy, the patient's clinical history and response to the protein, the type of protein used, and the discretion of the attending physician. The protein is suitably administered to the patient at one time or over a series of treatments and may be administered to the patient at any time from diagnosis onwards. The protein may be administered as the sole treatment or in conjunction with other drugs or therapies useful in treating the condition in question.

Where the protein of choice is an antibody, from about 0.1-20 mg/kg is an initial candidate dosage for administration to the patient, whether, for example, by one or more separate administrations. However, other dosage regimens may be useful. The progress of this therapy is easily monitored by conventional techniques.

Uses for an anti-IgE formulation (e.g., rhuMAbE-25, rhMAbE-26) include the treatment or prophylaxis of IgE-mediated allergic diseases, parasitic infections, interstitial cystitis and asthma, for example. Depending on the disease or disorder to be treated, a therapeutically effective amount (e.g. from about 1-15 mg/kg) of the anti-IgE antibody is administered to the patient.

E. Articles of Manufacture

In another embodiment of the invention, an article of manufacture is provided which contains the formulation and preferably provides instructions for its use. The article of manufacture comprises a container. Suitable containers include, for example, bottles, vials (e.g. dual chamber vials), syringes (such as dual chamber syringes) and test tubes. The container may be formed from a variety of materials such as glass or plastic. The container holds the lyophilized formulation and the label on, or associated with, the container may indicate directions for reconstitution and/or use. For example, the label may indicate that the lyophilized formulation is reconstituted to protein concentrations as described above. The label may further indicate that the formulation is useful or intended for subcutaneous administration. The container holding the formulation may be a multi-use vial, which allows for repeat administrations (e.g. from 2-6 administrations) of the reconstituted formulation. The article of manufacture may further comprise a second container comprising a suitable diluent (e.g. BWFI). Upon mixing of the diluent and the lyophilized formulation, the final protein concentration in the reconstituted formulation will generally be at least 50 mg/ml. The article of manufacture may further include other materials desirable from a commercial and user standpoint, including other buffers, diluents, filters, needles, syringes, and package inserts with instructions for use.

The invention will be more fully understood by reference to the following examples. They should not, however, be construed as limiting the scope of the invention. All citations throughout the disclosure are hereby expressly incorporated by reference.

Example 1

The effects of protein concentrations on the viscosity of a recombinant anti-IgE monoclonal antibody formulation (rhuMAb E25) were studied at 25° C. This antibody is a humanized anti-IgE monoclonal antibody that has been developed by Genentech Inc. as a potential therapeutic agent to treat allergic rhinitis and allergic asthma (Presta et al., *J. Immunol.* 151(5): 2623-2632 (1993)(PCT/US92/06860). The formulated rhuMAb E25 was formulated to a final concentration of 40 mg/ml, 85 mM Sucrose, 5 mM Histidine, 0.01% Polysorbate 20 and filled into 5 cc vials. The samples were then frozen from 5° C. to −50° C. in 45 minutes and followed by a sequential increase in the lyophilizer shelf temperature 10° C. per hour from −50° C. to 25° C. A drying step was conducted at a shelf temperature of 25° C. and a chamber pressure of 50 mTorr for 39 hours. The lyophilized rhuMAb E25 was reconstituted with SWFI to produce a solution with rhuMAb E25 at 125 mg/ml, 266 mM sucrose, 16 mM histidine, 0.03% polysorbate 20.

The viscosity of reconstituted samples were measured in Cannon-Fenske Routine capillary viscometer (Industrial Research Glassware LTD). The samples were measured approximately at 8 ml with a glass pipette and loaded into a capillary viscometer of size 50 for liquid samples with kinematic viscosity ranging from 0.8 to 4 cs or size 200 for those ranging from 20 to 100 cs. The sample temperature was maintained at 25° C. in a waterbath with a digitized temperature control system. The viscometer was placed into the holder vertically and inserted into the waterbath that was maintained at a fixed temperature. The efflux time was measured by allowing the liquid sample to flow freely down past marks. The kinematic viscosity of liquid sample in centistokes was calculated by multiplying the efflux time in seconds by the viscometer constants (0.004 for size 50 and 0.015 for size 100). The viscosity of E25 solution is highly dependent on the concentration of protein molecules (FIG. 1). It increases exponentially with increase of rhuMAb E25 concentration. At 25° C., the reconstituted rhuMAb E25 at 125 mg/ml is about 80 fold more viscous than water.

Example 2

The lyophilized rhuMAb E25 of Example 1 was reconstituted with different concentrations of NaCl solution. The viscosity of reconstituted solution was measured at 25° C. in a Cannon-Fenske Routine capillary viscometer using the same method as described in Example 1.

The results as shown in FIG. 2 demonstrate that the addition of NaCl can significantly reduce the viscosity of the protein formulation. The reconstituted rhuMAb E25 with 100 mM NaCl will give the solution that is about 4 fold less viscous than that reconstituted with SWFI.

The preparation of a rhuMAb E25 lyophilized formulation with 100 mM NaCl resulted in a slightly hypertonic solution. However, as reported previously, strict isotonicity is not absolutely necessary in that tissue damage was detected only when at extremely high tonicity levels (1300 mOsmol/Kg).

Thus, the administration of a formulation containing higher concentration of salt (100 mM to 200 mM NaCl resulting in osmolarity of ~600 to ~700 mOsmol/Kg for current rhuMAb E25 lyophilized materials) as contemplated herein, for reducing the viscosity of the formulation, does not appear to present a risk of tissue damage at the site of administration.

Example 3

The effects of different salts on the viscosity of rhuMAb E25 solution were studied at 25° C. The lyophilized rhuMAb E25 was first reconstituted with SWFI to produce a solution with rhuMAb E25 at 125 mg/ml, 266 mM sucrose, 16 mM histidine, 0.03% Polysorbate 20. The samples were then diluted with 10 mM histidine, 250 mM sucrose, pH 6.0 to a final concentration of 40 mg/ml. Various concentrated salts were then added into solution to bring the final salt concentration ranging from 0-200 mM. The viscosity of solution was determined in a Cannon-Fenske Routine capillary viscometer using the same method as described in Example 1.

The results were demonstrated in FIG. 3. Although each salt shows slightly different impact on change of viscosity, they appear to follow a similar trend whereby the viscosity of the solution decreases with increase in buffer concentration and ionic strength.

Example 4

Also studied were the effects of different buffers on viscosity of rhuMAbE25 solution at 25° C. A liquid formulation containing 80 mg/ml of rhuMAb E25, 50 mM histidine, 150 mM trehalose and 0.05% of Polysorbate 20 was added with different amounts of histidine, acetate, or succinate buffer components. The pH of sample was maintained at ~6.0 for all the preparation. The viscosity of solution was determined in a Cannon-Fenske Routine capillary viscometer using the same method as described in Example 1.

As shown in FIG. 4, the viscosity of solution containing either histidine or acetate buffers decreases with increasing buffer concentration up to 200 mM. However, for succinate buffer, the viscosity of solution decreases only at low buffer concentration (<100 mM), but not at high buffer concentration (>200 mM). Similar results have also been observed in other buffers that contain negatively charged multivalent buffer components, such as phosphate, citrate and carbonate.

Example 5

This example used a second generation of anti-IgE monoclonal antibody, rhuMAb E26. This monoclonal antibody is a homologous to rhuMAb E25 with five amino acid residue differences in CDR I region in the light chain and is described in WO 99/01556. The recombinant rhuMAb E26 was also expressed in CHO cell line and purified with similar chromatography methods as described above for rhuMAb E25. The samples were formulated into 5 mM histidine and 275 mM sucrose with concentration of rhuMAb E25 at 21 mg/ml. The viscosity of samples was measured at 6° C. in a Cannon-Fenske Routine capillary viscometer using the same method as described in Example 1.

The effects of NaCl on viscosity of rhuMAb E26 were shown in FIG. 5. The result demonstrates that the increase of NaCl concentration can effectively reduce the viscosity of rhuMAb E26 solution.

Example 6

The effects of pH on viscosity of a highly concentrated anti-IgE monoclonal antibody, rhuMAb E25 in liquid formulations have been examined in both hypotonic and isotonic conditions. The hypotonic solutions were prepared by adding small amounts of 10% acetic acid or 0.5M arginine into an unbuffered rhuMAb E25 solution that has been concentrated to ~130 mg/ml in Milli-Q water. The final concentrations of total buffer and salt were maintained at 17.5 mM. The hypotonic solutions were then mixed with a small volume of 5M NaCl to produce the isotonic solutions with final NaCl concentration around 150 mM NaCl. The viscosity of solution was determined at 25° C. in a Cannon-Fenske Routine capillary viscometer using the same method as described in Example 1. As shown in FIG. 6, the viscosity of rhuMAb E25 solution is highly dependent on the pH of buffer, especially in very hypotonic solutions. The addition of ionic species, such as NaCl, can significantly reduce such pH effects.

Example 7

The effects of pH on viscosity of a reconstituted anti-IgE monoclonal antibody, rhuMAb E25 have also been examined in the presence of other excipients, such astrehalose. The lyophilized rhuMAb E25 was reconstituted with SWFI and then dialyzed against 20 mM Histidine, 250 mM Trehalose, at pH 5. The protein concentration is about 94 mg/ml. The pH of solution was adjusted with 1M NaOH. The viscosity of solution was determined at 25° C. in a Cannon-Fenske Routine capillary viscometer using the same method as described in Example 1. The results, as shown in FIG. 7, demonstrated that the viscosity of antibody can be significantly altered by pH of solution.

What is claimed is:

1. A stable liquid formulation comprising a protein in an amount of at least about 80 mg/ml and a pharmaceutically acceptable acid, base or buffer in an amount of at least about 50 mM, so as to have either a pH of about 4.2 to about 4.9 or about 7.1 to about 12.0 and having a kinematic viscosity of about 50 cs or less at 25° C.

2. An article of manufacture comprising a syringe containing a stable liquid formulation comprising a monoclonal antibody in an amount of about 80-300 mg/ml and a pharmaceutically acceptable acid, base, or buffer in an amount of about 150-200 mM, wherein the acid, base, or buffer is comprised of arginine or histidine, and wherein the formulation has a kinematic viscosity of about 50 cs or less at 25° C.

3. The article of manufacture of claim 2, wherein the syringe is further contained within an injection device.

4. The article of manufacture of claim 2, wherein the acid, base, or buffer is arginine hydrochloride.

5. The article of manufacture of claim 2, wherein the acid, base, or buffer is in an amount of about 150 mM.

6. The article of manufacture of claim 2, wherein the acid, base, or buffer is in an amount of about 200 mM.

7. The article of manufacture of claim 2, wherein the antibody is in an amount of about 90-150 mg/ml.

8. The article of manufacture of claim 2, wherein the antibody is in an amount of about 150 mg/ml.

9. The article of manufacture of claim 2, wherein the formulation has a viscosity of about 40 cs or less.

10. The article of manufacture of claim 2, wherein the formulation has a viscosity of about 30 cs or less.

11. The article of manufacture of claim 2, wherein the formulation has a viscosity of about 20 cs or less.

12. The article of manufacture of claim 2, wherein the formulation has a viscosity of about 10 to 30 cs.

13. The article of manufacture of claim 2, wherein the formulation further comprises a lyoprotectant.

14. The article of manufacture of claim 13, wherein the lyoprotectant is a sugar.

15. The article of manufacture of claim 14, wherein the sugar is sucrose or trehalose.

16. The article of manufacture of claim 14, wherein the formulation comprises said sugar in an amount of about 60-300 mM.

17. The article of manufacture of claim 2, wherein the formulation further comprises a surfactant.

18. The article of manufacture of claim 2, wherein the formulation is hypertonic.

19. The article of manufacture of claim 2, wherein the formulation is a reconstituted formulation.

20. The article of manufacture of claim 19, wherein the antibody concentration in the reconstituted formulation is about 2-40 times greater than the antibody concentration in the mixture before lyophilization.

21. The article of manufacture of claim 2, wherein the antibody is directed against IgE.

22. The article of manufacture of claim 21, wherein the antibody is rhuMAb-E25, rhuMAb-E26 or rhuMAb-E27.

23. The article of manufacture of claim 2, further comprising directions for administration of said formulation.

24. The article of manufacture of claim 23, wherein the directions indicate use for the treatment or prophylaxis of an IgE-mediated disorder.

25. The article of manufacture of claim 24, wherein the disorder is asthma.

26. A stable liquid formulation comprising a monoclonal antibody in an amount of about 80-300 mg/ml and a pharmaceutically acceptable acid, base, or buffer in an amount of about 150-200 mM, wherein the acid, base, or buffer is comprised of arginine or histidine, wherein the formulation has a kinematic viscosity of about 50 cs or less at 25° C.

27. The formulation of claim 26, wherein the acid, base, or buffer is in an amount of about 150 mM.

28. The formulation of claim 26, wherein the acid, base, or buffer is in an amount of about 200 mM.

29. The formulation of claim 1 comprising said acid, base or buffer in an amount of at least about 100 mM.

30. The formulation of claim 1 comprising said acid, base or buffer in an amount of about 50-200 mM.

31. The formulation of claim 1 comprising said acid, base or buffer in an amount of about 100-200 mM.

32. The formulation of claim 1 comprising said acid, base or buffer in an amount of about 200 mM.

33. The formulation of claim 1 wherein said acid, base or buffer is selected from the group consisting of: acetic acid, hydrochloric acid, arginine and histidine.

34. The formulation of claim 1, wherein the base is derived from a base forming metal selected from the group consisting of lithium, sodium, potassium, calcium, magnesium, aluminum, zinc, iron, and copper.

35. The formulation of claim 1, wherein the base forming amine is $NR_4^+$ wherein $R_4$ is independently H or $C_{1-4}$ alkyl.

36. The formulation of claim 1 wherein the base or buffer is derived from an amino acid.

37. The formulation of claim 1, wherein the formulation has a viscosity of about 40 cs or less.

38. The formulation of claim 1, wherein the formulation has a viscosity of about 30 cs or less.

39. The formulation of claim 1, wherein the formulation has a viscosity of about 20 cs or less.

40. The formulation of claim 1, wherein the formulation has a viscosity of about 10 to 30 cs.

41. The formulation of claim 1 further comprising a lyoprotectant.

42. The formulation of claim 41 wherein said lyoprotectant is a sugar.

43. The formulation of claim 42 wherein said sugar is sucrose or trehalose.

44. The formulation of claim 42 comprising said sugar in an amount of about 60-300 mM.

45. The formulation of claim 1 further comprising a surfactant.

46. The formulation of claim 1, wherein the formulation is hypertonic.

47. The formulation of claim 1, wherein the formulation is a reconstituted formulation.

48. The formulation of claim 47 wherein the protein concentration in the reconstituted formulation is about 2-40 times greater than the protein concentration in the mixture before lyophilization.

49. The formulation of claim 1 wherein said protein has a molecular weight of at least about 15-20 kD.

50. The formulation of claim 1 wherein said protein is a member of the immunoglobulin gene superfamily.

51. The formulation of claim 50 wherein said protein is an immunoglobulin.

52. The formulation of claim 51 wherein said immunoglobulin is an antibody directed against a specific antigen.

53. The formulation of claim 52 wherein said antibody is directed against IgE, a member of the HER receptor family, a cell adhesion molecule or a subunit thereof, or a growth factor.

54. The formulation of claim 53 wherein the antibody is rhuMAb-E25, rhuMAb-E26 or rhuMAb-E27.

55. The formulation of claim 1, wherein the formulation is a liquid pharmaceutical formulation.

56. The formulation of claim 55, wherein the formulation is for subcutaneous administration.

57. The formulation of claim 1, wherein the acid, base or buffer is arginine hydrochloride.

58. The formulation of claim 26, wherein the acid, base or buffer is arginine hydrochloride.

* * * * *